(12) United States Patent
Makihira et al.

(10) Patent No.: US 9,170,087 B2
(45) Date of Patent: Oct. 27, 2015

(54) OPTICAL COHERENCE TOMOGRAPHY IMAGING APPARATUS, IMAGING SYSTEM, AND CONTROL APPARATUS AND CONTROL METHOD FOR CONTROLLING IMAGING RANGE IN DEPTH DIRECTION OF OPTICAL COHERENCE TOMOGRAPHY

(71) Applicant: CANON KABUSHIKI KAISHA, Tokyo (JP)

(72) Inventors: Tomoyuki Makihira, Tokyo (JP); Kazuhide Miyata, Yokohama (JP); Makoto Sato, Tokyo (JP); Yoshihiko Iwase, Kyoto (JP); Kazuro Yamada, Kawasaki (JP); Ritsuya Tomita, Kawasaki (JP); Yohei Minatoya, Yokohama (JP); Daisuke Kibe, Chigasaki (JP); Hiroyuki Shinbata, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 184 days.

(21) Appl. No.: 13/850,567

(22) Filed: Mar. 26, 2013

(65) Prior Publication Data
US 2013/0258349 A1    Oct. 3, 2013

(30) Foreign Application Priority Data

Mar. 30, 2012   (JP) ................................ 2012-082685

(51) Int. Cl.
*G01B 11/02*   (2006.01)
*G01B 9/02*    (2006.01)

(52) U.S. Cl.
CPC .................................. *G01B 9/02015* (2013.01)

(58) Field of Classification Search
CPC .... A61B 3/12; A61B 3/1233; G01B 9/02004; G01B 9/02091
USPC ................................................... 356/479, 497
See application file for complete search history.

(56) References Cited

U.S. PATENT DOCUMENTS

| | | | |
|---|---|---|---|
| 5,321,501 A | 6/1994 | Swanson et al. | |
| 8,559,016 B2* | 10/2013 | Nebosis | 356/497 |
| 2005/0219544 A1* | 10/2005 | Chan et al. | 356/497 |
| 2011/0267583 A1* | 11/2011 | Hayashi | 351/206 |
| 2012/0140172 A1* | 6/2012 | Torii et al. | 351/206 |

FOREIGN PATENT DOCUMENTS

| | | |
|---|---|---|
| JP | 2008154941 A | 7/2008 |
| JP | 2009244207 A | 10/2009 |
| JP | 2010158265 A | 7/2010 |

\* cited by examiner

*Primary Examiner* — Jonathan Hansen
(74) *Attorney, Agent, or Firm* — Canon USA Inc., IP Division

(57) ABSTRACT

An optical coherence tomography imaging apparatus that acquires a tomographic image from interference light between a reference beam and a measuring beam obtained via an object includes a control unit configured to control a difference in optical path length between the reference beam and the measuring beam by a control method according to an imaging target region, and a signal processing unit configured to generate image data of the object based on an electrical signal obtained by detecting the interference light with the difference in optical path length controlled by the control method.

18 Claims, 15 Drawing Sheets

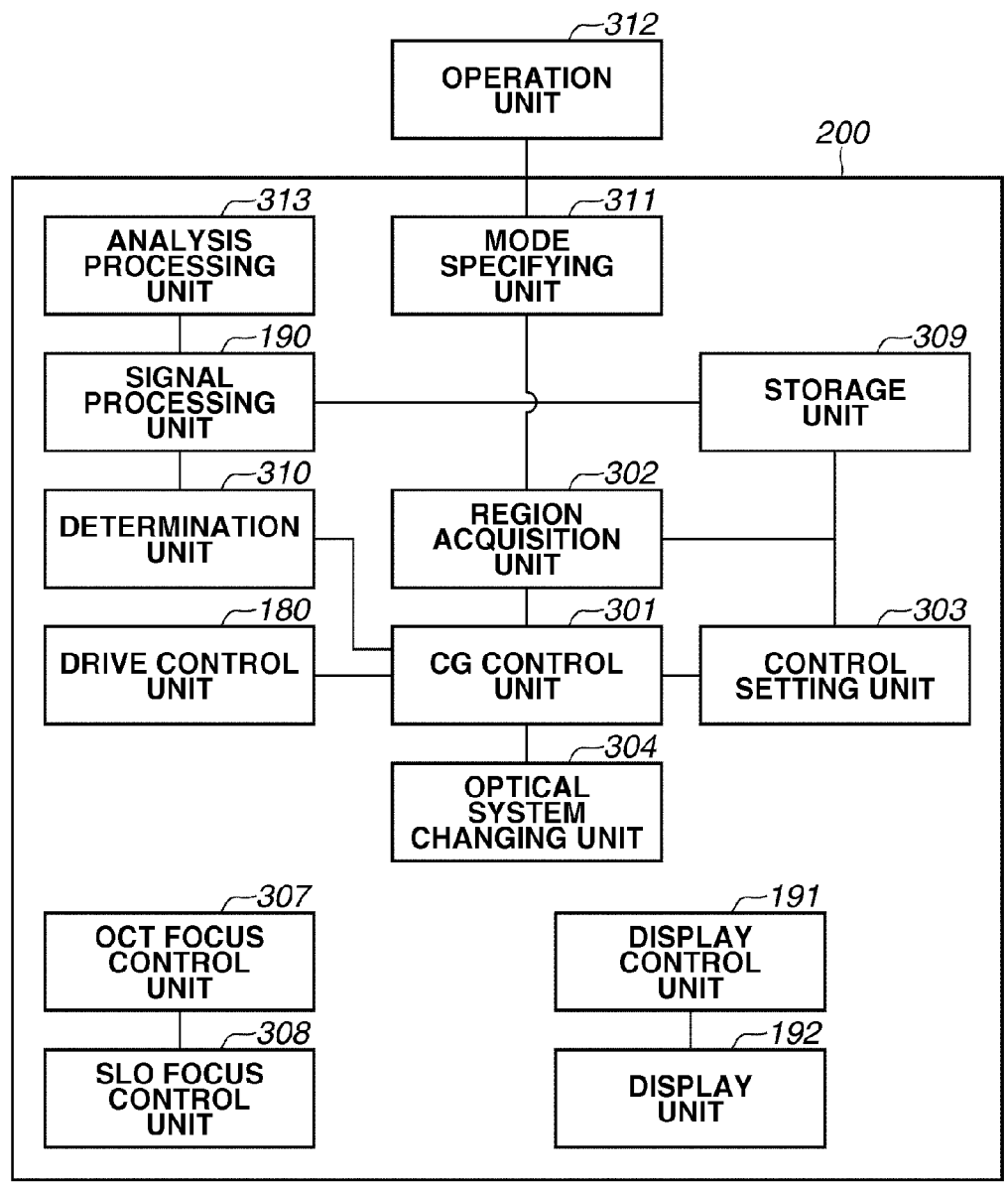

OPTICAL COHERENCE TOMOGRAPHY IMAGING APPARATUS, IMAGING SYSTEM, AND CONTROL APPARATUS AND CONTROL METHOD FOR CONTROLLING IMAGING RANGE IN DEPTH DIRECTION OF OPTICAL COHERENCE TOMOGRAPHY

BACKGROUND OF THE INVENTION

1. Field of the Invention

This disclosure relates to an optical coherence tomography imaging apparatus, an imaging system, and a control apparatus and a control method for controlling an imaging range in a depth direction of an optical coherence tomography.

2. Description of the Related Art

An ophthalmic tomographic imaging apparatus such as an optical coherence tomography (OCT) enables three-dimensionally observing a state inside a tissue such as a retinal layer, for example. A time domain (TD)-OCT in which a broad band light source is combined with a Michelson interferometer, for example, has been known as a form of the OCT. The TD OCT acquires information about depth resolution by measuring interference light between the backscattering lights of a reference arm and a signal arm while changing the optical path of the reference arm. There has also been known a spectral domain (SD)-OCT in which a spectroscope is used instead of changing the optical path of the reference arm and the spectral light is detected by a line sensor to acquire an interferogram. Furthermore, there has been known a swept source (SS)-OCT using a method in spectral interference is measured by a single channel optical detector using a high-speed wavelength-swept light source as a light source (refer to U.S. Pat. No. 5,321,501).

In the OCT, the smaller the difference in optical path length between a reference beam and a measuring beam becomes, that is, the nearer the optical path length becomes to the same position (the coherence gate position), the better image quality can be obtained. Japanese Patent Application Laid-Open 2008-154941 discusses that the difference in optical path length between the reference beam and the measuring beam is changed according to a signal to noise ratio (SN) of an image.

However, a method for controlling the difference in optical path length is not necessarily suited to an imaging target object, so that an imaging range cannot be quickly set.

SUMMARY OF THE INVENTION

According to an aspect of the present invention, an optical coherence tomography imaging apparatus that acquires a tomographic image from interference light between a reference beam and a measuring beam obtained via an object includes a control unit configured to control a difference in optical path length between the reference beam and the measuring beam by a control method according to an imaging target region, and a signal processing unit configured to generate image data of the object based on an electrical signal obtained by detecting the interference light with the difference in optical path length controlled by the control method.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 3 is a block diagram illustrating a detailed configuration of a control unit.

DESCRIPTION OF THE EMBODIMENTS

Various exemplary embodiments, features, and aspects of the invention will be described in detail below with reference to the drawings.

Figure 1:
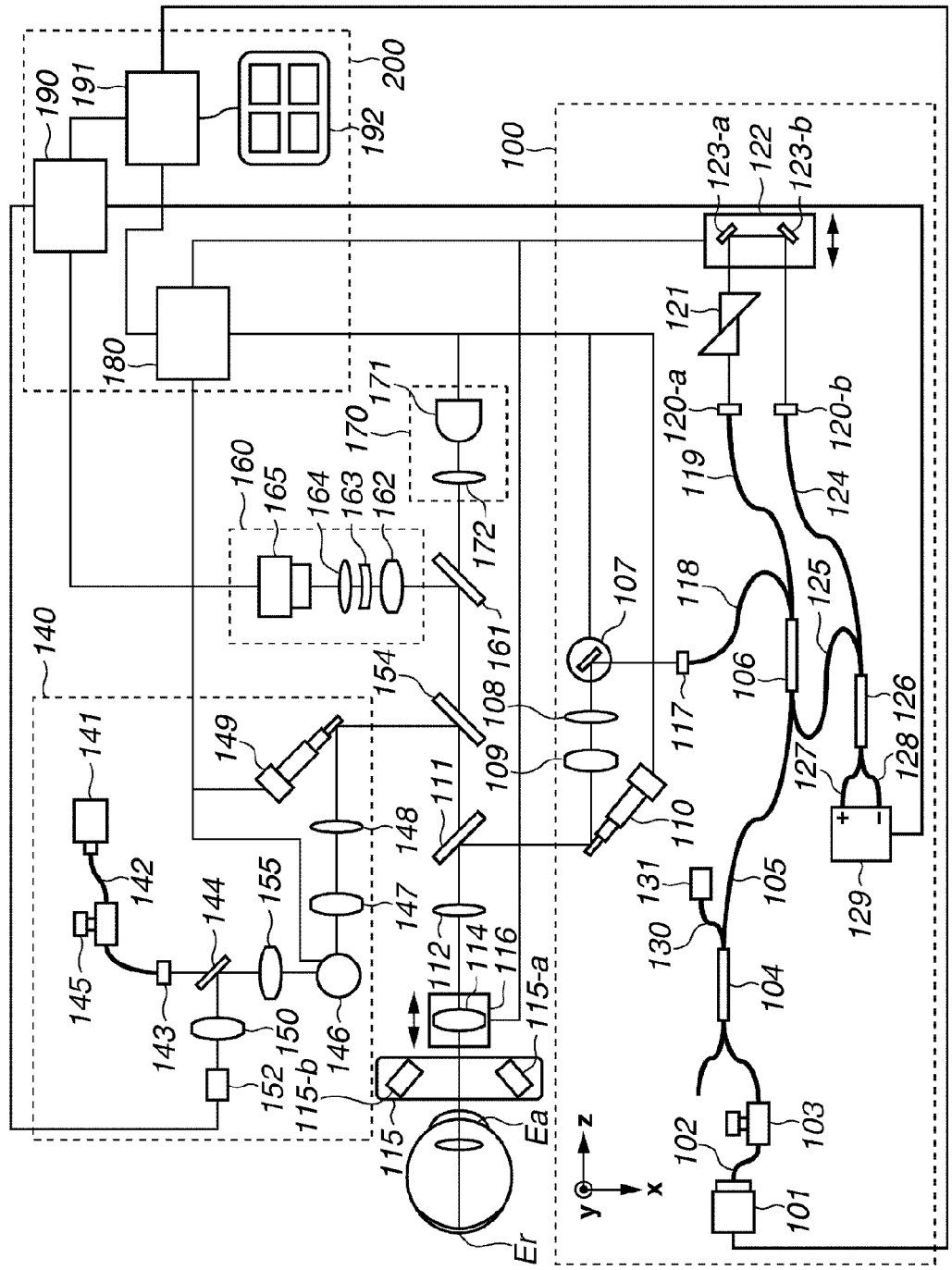
FIG. 1 is a diagram illustrating a general configuration of an optical coherence tomography imaging apparatus according to an exemplary embodiment of the present invention.

FIG. 1 illustrates a configuration of an optical coherence tomography imaging apparatus according to an exemplary embodiment of the present invention. The optical coherence tomography imaging apparatus according to the present exemplary embodiment is the one that light from a wavelength-swept light source is divided into a reference beam and a measuring beam passing through an object to acquire a tomographic image from interference light of the two beams. The optical coherence tomography imaging apparatus according to the present exemplary embodiment includes an SS-OCT (hereinafter referred to as OCT) 100, a scanning laser ophthalmoscope (referred to as SLO) 140, an anterior segment imaging unit 160, an internal fixation lamp 170, and a control unit 200.

The apparatus is aligned using the image of the anterior segment of a subject's eye observed by the anterior segment imaging unit 160 with the subject's eye fixed on the lighted internal fixation lamp 170. After the alignment is ended, a fundus is imaged by the OCT 100 and the SLO 140.

The OCT 100 functions as an imaging unit for capturing a tomographic image by scanning an imaging target region in the subject's eye with light from a wavelength-swept light source. The configuration of the OCT 100 is described below.

A light source 101 is a wavelength-swept light source capable of varying a wavelength and emits light whose center wavelength is 1040 nm and bandwidth is 100 nm, for example. The light emitted from the light source 101 is conducted to a fiber coupler 104 via a fiber 102 and a polarization controller 103 and branched to a fiber 130 for measuring light quantity and a fiber 105 for measuring OCT. The light emitted from the light source 101 is measured by a power meter (PM) 131 via the fiber 130. The light is conducted to a second fiber coupler 106 via the fiber 105. The second fiber coupler 106 functions as a division unit which divides an optical path for transmitting the light emitted from the light source 101 into a reference optical path and a measuring optical path. Thereby, the light emitted from the light source 101 is branched into a measuring beam (also referred to as an OCT measuring beam) and a reference beam. The polarization controller 103 is the one that adjusts the state of polarization of the light emitted from the light source 101 and adjusts it to linear polarization. The branching ratio of the fiber coupler 104 is 99:1 and the branching ratio of the fiber coupler 106 is 90 (reference beam):10 (measuring beam).

The measuring beam branched by the fiber coupler 106 is emitted from a collimator 117 as parallel light via a fiber 118. The emitted light reaches a dichroic mirror 111 via an X scanner 107 formed of a galvano-mirror which scans the measuring beam in the horizontal direction at the fundus Er, lenses 108 and 109, and a Y scanner 110 formed of a galvano-mirror which scans the measuring beam in the vertical direction at the fundus Er. The X and Y scanners 107 and 110 are driven by a drive control unit 180 to allow the measuring beam to scan an area with a predetermined range at the fundus Er. The dichroic mirror 111 has a characteristic which reflects light with wavelength from 950 nm to 1100 nm and transmits light with wavelengths other than those.

The measuring beam reflected by the dichroic mirror 111 reaches a focus lens 114 mounted on a stage 116 via a lens 112. For an imaging mode in which the retinal layer of the fundus is tomographically imaged, the focus lens 114 for the measuring beam is focused on the retinal layer of the fundus Er via the anterior segment Ea of a subject's eye. The measuring beam incident on the fundus Er is reflected and scattered by each retinal layer and returned to the fiber coupler 106 via the above optical path. The measuring beam returned from the fundus Er reaches a fiber coupler 126 via the fiber coupler 106 and a fiber 125. For an imaging mode in which the anterior segment Ea is tomographically imaged, the focus lens 114 is focused not on the fundus Er but on a predetermined region of the anterior segment Ea. Focusing on the anterior segment Ea can be adjusted by moving the position of the focus lens 114 or by an optical component such as a dedicated lens inserted into the optical path across the focus lens 114. In this case, the optical component can be detached from the optical path by a driving unit. When the anterior segment imaging mode is selected, the driving unit inserts the optical component into the optical path. When the fundus imaging mode is selected, the driving unit causes the optical component to retreat from the optical path.

The reference beam branched by the fiber coupler 106 is emitted as parallel light via a fiber 118 from a collimator 120-a. The emitted reference beam passes through a dispersion compensation glass 121, is reflected by reference mirrors 123-a and 123-b on a coherence gate stage 122, and reaches the fiber coupler 126 via a collimator 120-b and a fiber 124.

The coherence gate stage 122 functions as a change unit for changing the position of the reference mirrors 123-a and 123-b and adjusts the optical path lengths of the measuring beam and the reference beam by such a function. The mirrors 123 is arranged so that imaging can be performed at a position where the optical path lengths of the measuring beam and the reference beam are equal to each other. The coherence gate stage 122 is controlled by the drive control unit 180 to react to a difference in an eye axial-length of the subject's eye. The control of the drive control unit 180 is described below.

The fiber coupler 126 functions as a light combination unit for combining the reference beam passing through the reference optical path with the measuring beam passing through the measuring optical path. Thus, the measuring beam and the reference beam reaching the fiber coupler 126 are combined with each other and translated into interference light. An interference signal is converted to an electric signal by a differential detector (balanced receiver) 129 which is an optical detector for detecting the combined light via fibers 127 and 128. The converted electric signal is analyzed by a signal processing unit 190.

The configuration of the SLO 140 is described below.

A light source 141 is a semiconductor laser and emits light with a center wavelength of 780 nm in the present exemplary embodiment. The measuring beam (also referred to SLO measuring beam) emitted from the light source 141 passes though a fiber 142, is adjusted into a linear polarization by a polarization controller 145, and emitted as parallel light from a collimator 143. The emitted measuring beam reaches a dichroic mirror 154 via a perforated portion of a perforated mirror 144, a lens 155, an X scanner 146 formed of a galvano-mirror which scans the measuring beam in the horizontal direction at the fundus Er, lenses 147 and 148, a Y scanner 149 formed of a galvano-mirror which scans the measuring beam in the vertical direction at the fundus Er. The X and Y scanners 146 and 149 are driven by the drive control unit 180 to allow the measuring beam to scan a predetermined range at the fundus Er. The dichroic mirror 154 has a characteristic which reflects light with wavelength from 760 nm to 800 nm and transmits light with wavelengths other than those.

The measuring beam of linear polarization reflected by the dichroic mirror 154 passes through the dichroic mirror 111 and the same optical path as that the OCT measuring beam of the OCT 100 passes through and reaches the fundus Er.

The SLO measuring beam incident on the fundus Er is reflected and scattered by the fundus Er, passes through the above optical path and reaches the perforated mirror 144. The light reflected by the perforated mirror 144 passes through a lens 150, is received by an avalanche photodiode (hereinafter referred to as APD) 152, converted into an electric signal and received by the signal processing unit 190.

The position of the perforated mirror 144 is conjugated with that of the pupil of the subject's eye. The light passing through the periphery of the pupil among the light beams in which the measuring beam incident on the fundus Er is reflected and scattered is reflected by the perforated mirror 144.

The anterior segment imaging unit 160 is described below.

In the anterior segment imaging unit 160, the anterior segment Ea is irradiated by an illumination light source 115 including light emitting diodes (LED) 115-a and 115-b for emitting illumination light with a wavelength of 850 nm. The light reflected by the anterior segment Ea passes through the lenses 114 and 112 and the dichroic mirrors 111 and 154 and reaches a dichroic mirror 161. The dichroic mirror 161 has a characteristic which reflects light with wavelength from 820 nm to 900 nm and transmits light with wavelengths other than those. The light reflected by the dichroic mirror 161 is received by an anterior segment camera 165 via lenses 162, 163, and 164. The light received by the anterior segment camera 165 is converted into an electric signal and received by the signal processing unit 190.

The internal fixation lamp 170 is described below.

The internal fixation lamp 170 includes a display unit 171 and a lens 172. The display unit 171 uses a plurality of light emitting diodes (LEDs) arranged in a matrix form. A position where the LED is emitted is changed by the control of the drive control unit 180 according to the region desired to be imaged. The light emitted from the internal fixation lamp 170 is guided to the subject's eye via the lens 172. The light emitted from the internal fixation lamp 170 has a wavelength of 520 nm and a desired pattern is displayed by the drive control unit 180.

Image generation and image analysis in the signal processing unit 190 are described below.

The signal processing unit 190 subjects each interference signal output from a differential detector 129 to general reconstruction processing to generate a tomographic image.

The signal processing unit 190 removes a fixed pattern noise from the interference signal. The fixed pattern noise is removed in such a manner that a plurality of detected A-scan signals is averaged to extract a fixed pattern noise and the fixed pattern noise is subtracted from the input interference signal.

The signal processing unit 190 performs window function processing to optimize a depth resolution and a dynamic range, which have a trade-off relation when Fourier transform is performed in a finite interval. Fast Fourier transform (FFT) processing is performed to generate a tomographic signal.

Figure 2A:
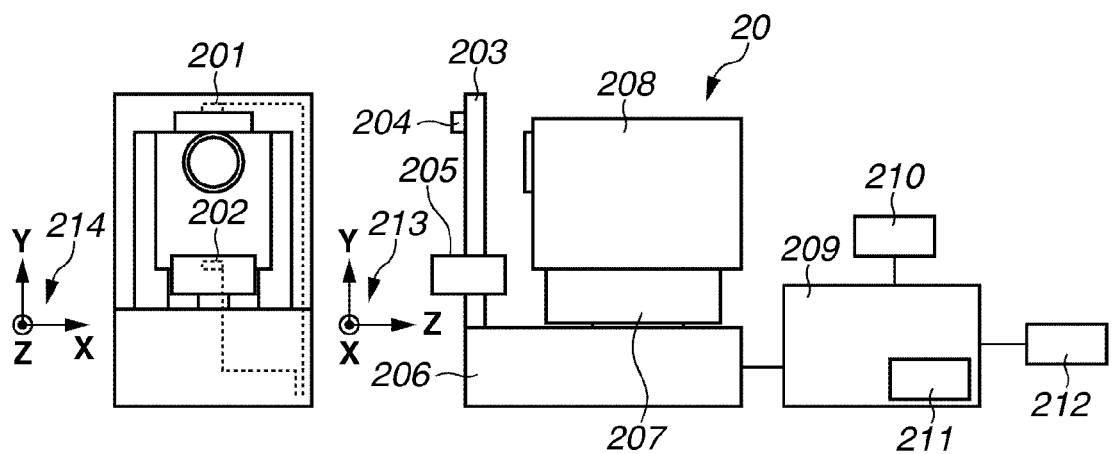
FIGS. 2A and 2B illustrate an external appearance of the optical coherence tomography imaging apparatus.
Figure 2B:
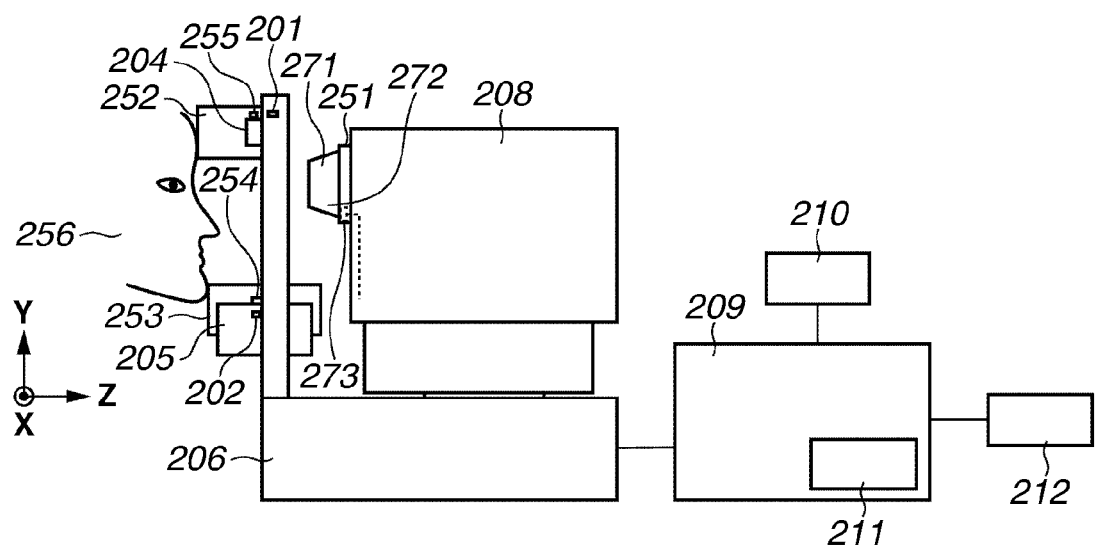

The switching of the imaging mode of the anterior and posterior segments is described based on external views illustrated in FIGS. 2A and 2B. In FIG. 2A, an optical coherence tomography imaging apparatus 20 is composed of a plurality of physical units. The OCT 100 can image light with a long wavelength using a variable-wavelength light source, so that the OCT 100 is suited for imaging not only an object small in thickness such as a retina of the fundus but also an object comparatively large in thickness such as an anterior segment. Even if a difference between the optical paths of SS-OCT measuring and reference beams is large, the OCT 100 can inhibit decrease in sensitivity, so that, in this respect, the OCT 100 is suited for imaging an object large in thickness. The use of the characteristic allows the SS-OCT to image both of the anterior and posterior segments.

In FIG. 2A, the optical coherence tomography imaging apparatus 20 includes an optical head 208, which is a measuring optical system for acquiring an anterior segment image, a two-dimensional fundus image, and a tomographic image, and a stage unit 207, which is a moving unit allowing the optical head 208 to be moved in the XYZ directions using a motor (not illustrated). The stage unit 207 functions as an alignment unit for changing a distance and a positional relationship between a subject's eye and the optical coherence tomography imaging apparatus 20. A base unit 206 contains a spectroscope described below. A personal computer 209 doubles as a control unit of the stage unit 207 and performs the construction of a tomographic image described below as well as the control of the stage unit 207. A hard disk 211 stores a program for capturing tomographic images in a subject information storage unit and an examination set storage unit. A monitor 210 is a display unit. An input unit 212 provides the personal computer 209 with instructions and is specifically made of a keyboard and a mouse. A face rest 203 fixes the subject's jaw and forehead to urge the subject' eye to be fixed. A silicone rubber member 204 is the one against which a subject's forehead is rested (hereinafter referred to as a forehead rest). A subject's jaw supporting member 205 is moved by an actuator (not illustrated) with a stroke of 30 mm in the Y direction to adjust the height of the subject's eye (hereinafter referred to as a jaw supporter). A Hall element 201 is attached to the inside of a housing above a mounting unit of the face-rest silicone rubber member 204. A Hall element 202 is also attached to the inside of the jaw supporting member 205. The Hall elements 201 and 202 are connected to a CPU substrate (not illustrated) attached to the inside of an ophthalmologic examination apparatus 200 to detect magnetism.

The jaw supporter and the forehead rest are examples of an attachment member and at least one of them has only to be used. The attachment members are attached to the ophthalmologic examination apparatus 200 to move the focus of the apparatus 200 with respect to the anterior segment.

FIG. 2B illustrates an example of the optical coherence tomography imaging apparatus to which an adapter unit for imaging the anterior segment is attached. An objective lens barrel 251 is attached thereto. A member 252 adjusts a focal position to the anterior segment of a subject 256 (hereinafter, the member 252 is referred to as an attachment forehead rest). The member 252 is made of silicone rubber. A magnet 255 is incorporated into the attachment forehead rest 252 and attached to the face rest 203 to cover the forehead rest 204. A surface fastener or an attaching/detaching mechanism, which are not illustrated, is provided to prevent the magnet 255 from being detached. The attachment of the magnet 255 to the face rest 203 to cover the forehead rest 204 causes the Hall element 201 to react to magnetism, and the CPU (not illustrated) arranged in the ophthalmologic examination apparatus 200 detects that the attachment forehead rest 252 is attached to a main body. A member 253 adjusts a focal position to the anterior segment of the subject 256 (hereinafter, the member 253 is referred to as an attachment jaw rest). The member 253 is made of silicone rubber. A magnet 254 is incorporated into the attachment jaw rest 253 and attached to the jaw supporter 205 to cover the jaw rest 253. The attachment jaw rest 253 covers the jaw supporter 205 to cause the Hall element 202 to react to magnetism, and the CPU (not illustrated) arranged in the optical coherence tomography imaging apparatus 20 detects that the attachment jaw rest is attached to the jaw supporter 205. A barrel 271 contains an anterior imaging lens. Therefore, an optical member attached in front of an objective lens as an attachment member is also included. The barrel 271 is screwed into a filter screw portion (not illustrated) of the objective lens barrel 251 so as to be attached to the optical coherence tomography imaging apparatus 20. A magnet 272 is incorporated into the vicinity of the filter screw of the barrel 271. A Hall element 273 is connected to a CPU (not illustrated) arranged in the optical coherence tomography imaging apparatus 20. When the Hall element 273 is screwed into a filter screw portion (not illustrated) of the objective lens barrel 271 so as to be attached to the optical coherence tomography imaging apparatus 20, the Hall element 273 reacts to the magnet 272 and the CPU (not illustrated) arranged in the optical coherence tomography imaging apparatus 20 detects that the barrel 271 is attached to the optical coherence tomography imaging apparatus 20. In the above description, the Hall element is used to detect the attachment members for imaging the anterior segment 252, 253, and 271. However, an electrostatic-capacity distance sensor or a switch sensor may be used to detect the attachment members.

A module area for determination in a sensor such as the Hall element for determining whether the attachment members are attached to the ophthalmologic apparatus 200 are attached and the CPU or the personal computer 209 for determining whether the attachment members are actually attached based on the signal acquired from the sensor collaboratively functions as an attachment detection unit for detecting whether the anterior segment imaging adapter member is attached. An imaging mode selection unit described below executes a determination as to whether the anterior segment imaging mode is selected. The optical members, as the attachment member in the present exemplary embodiment, attached to the subject's eye side of the objective lens in the optical path of the measuring beam are also cited as examples. The attachment detection unit always monitors the detection of attachment/detachment and properly notifies the control unit 200 of the detection result of attachment/detachment and, if a change occurs in detection result, the attachment detection unit notifies the control unit 200 each time it happens.

The above configuration enables detecting whether the anterior segment imaging adapter is attached.

The detailed configuration of the control unit 200 is described with reference to FIG. 3.

The control unit 200 includes a coherence gate (CG) control unit 301 for controlling a difference in optical path length between the reference beam and the measuring beam (coherence gate) by a control method according to an imaging target region. A fine adjustment of the coherence gate may not be needed because a signal is less attenuated depending on an object or adjustment itself may not be needed. A method for controlling a difference in optical path length between the reference beam and the measuring beam is changed according to an imaging target region and the difference is controlled by the CG control unit 301 using this character to allow a quick adjustment without consuming unnecessary adjustment time.

For a first imaging target region, the CG control unit 301 controls the difference in optical path length so that the difference is made equal to a predetermined value. For a second imaging target region, the CG control unit 301 controls the difference in optical path length based on the signal of interference light. When the anterior segment is imaged as the first imaging target region, for example, attenuation in the measuring beam due to the object is small, so that there is sometimes no need for searching for an appropriate position of the coherence gate. Therefore, the control of the difference in optical path length using a value stored according to a subject or a value set for a standard subject allows an image good enough in image quality to be acquired. When the fundus (posterior segment) is imaged as the second imaging target region, a signal is significantly attenuated and an object is comparatively small in thickness, so that the coherence gate needs to be appropriately adjusted. When the anterior segment is imaged, the CG control unit 301 performs control so as to set the difference in optical path length to a predetermined initial value to adjust the coherence gate using this character.

When the posterior segment is imaged, the CG control unit 301 controls the coherence gate stage 122 to search for a position as an appropriate difference in optical path length while moving the reference mirror 123. The signal processing unit 190 generates the image data of the object by a control method according to a region based on an electric signal acquired by detecting interference light in a state where the difference in optical path length is controlled. This provides a posterior segment tomographic image good in image quality. The CG control unit 301 can make compatible quickly imaging and acquiring an image good in image quality. In particular, when the subject's eye is imaged, forcing a subject to fixate for a long time puts a heavy burden on the subject, which needs to decrease the time for adjustment for imaging. The omission of the adjustment conforms to such a demand. The reduction of an imaging cycle improves a medical efficiency.

A feedback control using image information can be used for searching for the difference in optical path length. A determination unit 310 moves the reference mirror 123 by a predetermined length, the signal processing unit 190 acquires a tomographic image with the reference mirror 123 moved, and the determination unit 310 determines whether the difference in optical path length between the reference beam and the measuring beam is appropriate. The CG control unit 301 performs control for repeating this processing to search for an appropriate position of the reference mirror 123, in other words, to search for an appropriate position of the difference in optical path length. Thus, information about the tomographic image acquired from the signal processing unit 190 can be fed back to search control of an appropriate difference in optical path length performed by the CG control unit 301 in imaging the posterior segment.

The determination unit 310 can use a luminance value of the tomographic image as a reference for determining whether the difference in optical path length is appropriate. In this case, the determination unit 310 determines whether the size of a representative value of a pixel value of image data is equal to or greater than a specific threshold. An average value or a medium value of the whole tomographic image is acquired as a representative value to determine whether the representative value reaches a predetermined threshold. The use of the representative value can simplify the determination processing and remove the influence of noises to allow the difference in optical path length to be accurately set.

The determination unit 310 can be caused to have a function to determine whether the adjustment of the difference in optical path length using an initial value is appropriate in imaging the anterior segment. If the difference in optical path length is controlled to get to a predetermined value with respect to the first imaging target region, the determination unit 310 determines whether the image data acquired from the signal processing unit 190 satisfies a specific reference. If the determination unit 310 determines that the image data does not satisfy the specific reference, the CG control unit 301 controls the difference in optical path length based on the interference light which can be acquired while sequentially changing the difference in optical path length. In other words, as long as the determination unit 310 determines that the adjustment using the initial value is not appropriately performed, the search control that is similar to that in the second imaging target region is performed. This allows surely adjusting the difference in optical path length in imaging the anterior segment.

For the first imaging target region (the anterior segment), the selection of a control method similar to the one in the second imaging target region allows surer adjustment. The control method applied to the first imaging target region is managed by a control setting unit 303. A correspondence relationship between the imaging target region and the control method is properly set according to a user's input via an operation unit 312. This allows adjustment according to a user's taste.

The change of a moving interval of the reference mirror 123 to be adjusted according to the imaging target region, as a method for controlling the difference in optical path length, allows adjustment corresponding to a difference in thickness particularly of the imaging target region. The CG control unit 301 sets the control method for determining the difference in optical path length to an imaging target region based on the signal of the coherence light acquired while sequentially varying the difference in optical path length at a first interval. The CG control unit 301 determines the difference in optical path length for another imaging target region based on the signal of the coherence light acquired while sequentially varying the difference in optical path length at a second interval smaller than the first interval. The control setting unit 303 sets any of the control methods according to information about the imaging target region. Thereby, in a region where a detailed search is less required, a search interval is increased to increase efficiency. In a region where the detailed search is required, the search interval is decreased to allow accuracy to be improved.

As another control method, the CG control unit 301 can control the difference in optical path length by two-stage adjustment of coarse and fine adjustment in a specific imaging target region. In this case, this uses a control method in which the CG control unit 301 determines a specific range of the difference in optical path length based on the signal of the coherence light acquired while sequentially varying the difference in optical path length at a specific interval (a second interval) and the difference in optical path length based on the signal of the coherence light acquired while sequentially varying the difference in optical path length in the specific range. The method is capable of efficiently adjusting the difference in optical path length in a region requiring a detailed adjustment like the posterior segment in particular.

Furthermore, there is a control method in which a coarse adjustment is performed at a first interval in the anterior segment, a coarse adjustment is performed at a second interval smaller than the first interval in the posterior segment, and a fine adjustment is performed thereon. This enables the control of the difference in optical path length in which efficiency and accuracy are compatible according to the characteristic of the anterior segment in the anterior segment, which is thick and less requires detailed adjustment. On the other hand, in the posterior segment, which is small in thickness and requires detailed adjustment, the control of the difference in optical path length in which efficiency and accuracy are compatible is enabled in consideration of such characteristic.

The CG control unit 301 can efficiently adjust the difference in optical path length using an initial value for controlling the difference in optical path length with respect to not only the anterior segment but the posterior segment or all imaging target regions. In this case, in a case where the reference mirror 123 is sequentially moved from the vicinity of the position corresponding to the initial value and an image whose image quality exceeds a reference is acquired, the CG control unit 301 regards the case as completing the adjustment of the difference in optical path length and stores the position corresponding to the reference mirror 123 in this case into a storage unit 309. Thereby, the search efficiency can be improved.

Initial values different for each imaging target region and imaging mode are stored and the initial values are selected according to information about the imaging target region to allow a quick adjustment according to regions. There is sometimes no need for adjusting in detail the difference in optical path length in the anterior segment, for example, so that a mean value or an experimentally obtained value near thereto with respect to the anterior segment and the posterior segment of a standard person may be stored as an initial value of the difference in optical path length. Thus, the initial value according to the imaging target region can be acquired. For the case of a continuous imaging mode that images the anterior segment and then the posterior segment, another initial value may be provided. If the difference in optical path length can be appropriately set in imaging the anterior segment, the difference in optical path length may include deviation from a standard value such as a working distance due to a personal difference. For this reason, the initial value is corrected with respect to the standard value by the CG control unit 301 or the control setting unit 303 in consideration of the deviation at the CG adjustment of the posterior segment. This can make continuous imaging more efficient. The initial value is stored for each imaging target region and imaging mode in the storage unit 309 to enable reuse thereof.

The initial value can be set according to the subject or both of the subject and the imaging target region. In this case, the storage unit 309 stores the value indicating the determined difference in optical path length for each subject or with information about both of the subject and the imaging target region associated with each other. This can improve an imaging efficiency in a case where particularly the same subject is repetitively imaged at spaced time intervals.

The initial value may be stored with the difference in optical path length between the reference beam and the measuring beam as a parameter. However, the amount of deviation in the reference mirror 123 and the coherence gate stage 122 from the reference position is stored to allow accurate adjustment according to the characteristics of the members.

The control method can be automatically set based on information about the imaging target region. The information about the imaging target region is specified according to a user's operation and acquired by a region acquisition unit 302. The acquired information about the imaging target region is input to the control setting unit 303. The control setting unit 303 sets the control method for the difference in optical path length between the reference beam and the measuring beam according to the imaging target region. The control setting unit 303 acquires the CG control method corresponding to the acquired imaging target region with reference to the storage unit 309 and notifies the CG control unit 301 of the setting. This enables the CG control unit 301 to select the control method according to the region.

In another example, the moving interval of the reference mirror for changing the difference in optical path length can be increased to the extent that the moving interval does not exceed the length corresponding to the thickness of the anterior segment using the anterior segment being comparatively greater in thickness.

Associating the information about the imaging target region with the imaging mode set by the user via the operation unit allows the user to quickly execute adjustment for a predetermined imaging only by setting the imaging mode. The imaging mode is specified via the operation unit 312. A mode specifying unit 311 receives an operation input from the operation unit 312 to specify the imaging mode. The imaging mode described here includes setting information about a plurality of imaging operations. For example, the information includes information about the imaging target region such as the anterior segment, the posterior segment, the cornea of the anterior segment, and the optic disk of the posterior segment, information about scan position of default setting of the OCT, and information about scanning method for radial scanning or XY scanning. The region acquisition unit 302 receives information about the imaging mode and extracts information about the imaging target region corresponding to the imaging mode with reference to a lookup table in the storage unit.

The mode specifying unit 311 can specify a continuous imaging mode for continuously imaging a plurality of imaging target regions. If an eye is imaged, an imaging mode for imaging both of the anterior segment and the posterior segment is available. In the imaging mode, as imaging of one of the anterior and posterior segments is ended, at least a part of imaging preparation for another is started. This enables the user to save the trouble of performing input operation for specifying the imaging mode every time for each imaging target region via the operation unit 312.

The mode specifying unit 311 can specify any of a first mode which is transferred to the imaging mode of the posterior segment as the imaging of the anterior segment is ended and a mode which is transferred to the imaging mode of the anterior segment as the imaging of the posterior segment is ended. An imaging sequence according to a diagnosis situation can be adopted such that, for example, a situation is confirmed in detail by an image in the other region after an abnormality is detected in any of the regions.

Furthermore, the mode specifying unit 311 can specify an automatic adjustment mode indicating whether an automatic adjustment is turned off.

The control unit 200 can be equipped with an optical system changing unit 304 for controlling a drive unit capable of inserting and retracting an optical system for imaging the anterior segment into and from an imaging optical system as illustrated in FIG. 3. The optical system changing unit 304 performs control so as to insert or retract an optical system (not illustrated) for correcting influence attributed to a difference in whether to pass through a crystalline lens into and from an imaging optical path when the imaging target region is switched between the anterior and posterior segments. This allows the user to save trouble in switching the imaging target region between the anterior and posterior segments to improve an imaging efficiency.

Furthermore, the drive control unit 180 of the control unit 200 generally controls moving control of each unit as described above. The drive control unit 180 of the control unit 200 sends a control value for moving the coherence gate stage 122 to the drive unit to control the position of the coherence gate stage 122.

An OCT focus control unit 307 controls the focus position of light emitted from the wavelength-swept light source. An SLO focus control unit 308 controls the focus position of the measuring beam of the SLO.

An analysis processing unit 313 extracts information useful for diagnosis from the acquired tomographic image. The analysis processing unit 313 calculates the thickness of a cornea and the magnitude of an angulus iridocorneals, for example, from the tomographic image of the anterior segment. The analysis processing unit 313 performs extraction processing of each layer of a retina from the tomographic image of the posterior segment. The analysis processing unit 313 performs the segmentation of the tomographic image using the above luminance image. In this case, the analysis processing unit 313 applies a median filter and a Sobel filter to the tomographic image to be processed to produce an image (hereinafter referred to as a median and a Sobel image). A profile is produced from the produced median and Sobel images for each A-scan. A profile of a luminance value is produced from the median image. A profile of gradient is produced from the Sobel image. A peak in the profile produced from the Sobel image is detected. A boundary in each area of a retinal layer is extracted with reference to the profile of the median image corresponding to across or between the detected peaks. The analysis processing unit 313 measures the thickness of each layer in the direction of A-scan line to produce a layer thickness map of each layer.

The analysis result acquired by the analysis processing unit 313 is displayed by a display control unit 191.

The display control unit 191 displays the image produced by the signal processing unit 190 and the analysis result on the display screen of a display unit 192. The display unit 192 displays variety of information as described below under the control of the display control unit 191.

The display unit 192 also displays information about the region acquired by the region acquisition unit 302. Thereby, if a plurality of adjustments is automatically performed, the user is caused to strongly recognize the imaging target region to allow the possibility of erroneous imaging to be reduced.

If the mode specifying unit 311 turns off the automatic adjustment of alignment, focus, and coherence gate, the mode specifying unit 311 also displays information about adjustment state of these adjustment items on the imaging screen. The term adjustment state indicates whether the adjustment of the adjustment items is completed or indicates an adjustment value such as a diopter value. The information about the adjustment state is acquired by the control unit 200. The control unit 200 acquires the adjustment values based on the control values from the stage unit 207 functioning as an alignment unit, the adapter detection units illustrated in FIG. 2, the OCT focus control unit 307, and the CG control unit 301. At least a plurality of adjustment states are displayed as an example of the adjustment state among: a distance between a subject's eye and the optical coherence tomography imaging apparatus; a positional relationship between the subject's eye and the optical coherence tomography imaging apparatus; focus position and coherence gate position; and the attachment status of the adapter unit detected by the adapter detection unit. The reason the plurality of adjustment items are displayed is that an already adjusted item can be shifted to a failure state in adjustment due to the movement of the subject's eye while adjustment is performed in turn. The display of the plurality of adjustment items is particularly effective for manual adjustment. The control unit 200 acquires determination results as to whether the determination unit 310 completes the adjustment based on the value output from the signal processing unit 190. Thus, the adjustment state about each adjustment item required for imaging is acquired.

If it is set that the adjustment is not automatically performed by the above processing, the display control unit 191 performs control so as to display information indicating that the adjustment of the adjustment items in which the determination unit 310 determines that the adjustment of the adjustment items related to setting is completed is completed. On the other hand, if it is set that the adjustment is automatically performed, it is less significant to notify the user of the adjustment state particularly about the completed adjustment items, so that display indicating that each adjustment state is completed is not performed in view of the effective use of a screen area and easy view of information. In other words, if it is set that the adjustment is automatically performed, the display control unit 191 does not cause the display unit to display information indicating that the adjustment of the adjustment items in which the determination unit 310 determines that the adjustment is completed is completed.

If the mode specifying unit 311 turns off the automatic adjustment of alignment, focus, and coherence gate, the control setting unit 303 instructs the stage unit 207 functioning as the alignment unit, the adapter detection units illustrated in FIG. 2, the focus control unit 307, and the CG control unit 301 not to perform automatic adjustment. The control setting unit 303 can perform setting as to whether to individually and automatically adjust a plurality of adjustment items. At this point, a determination as to whether to complete the adjustment does not need to be ended while controlling not to automatically perform the adjustment. Needless to say, the control setting unit 303 can instruct the determination unit 310 not to perform determination processing.

The display control unit 191 causes the display unit 192 to display the attachment state of the adapter units for imaging the anterior segment according to attachment and detachment. At this point, the imaging target region can be identified as the anterior segment according to the detection of attachment of the anterior-segment adapter. In this case, if the anterior-segment adapter is attached, the region acquisition unit 302 automatically takes the imaging target region as the anterior segment. Notwithstanding the mode specifying unit 311 specifying the anterior segment imaging mode, the attachment of the adapter unit can be detected. Thus, if the adjustment state is different from mode information such as region information specified by the user, the display control unit 191 can issue warning information.

If a necessary adjustment is completed but an appropriate imaging cannot be performed in the adjustment state, the display control unit 191 causes the display unit 192 to display information about an imaging target region. If adjustment is insufficient, the display control unit 191 causes the display unit 192 not to display information about an imaging target region. The determination unit 310 determines whether the adjustment state in which the tomographic image of the imaging target region can be imaged by the OCT 100 is kept.

Figure 4A:
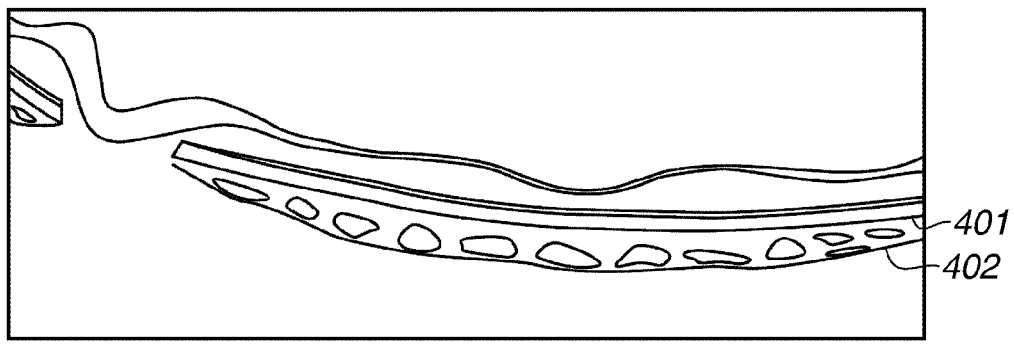
FIGS. 4A, 4B, and 4C illustrate examples of tomographic images captured by the OCT.
Figure 4B:
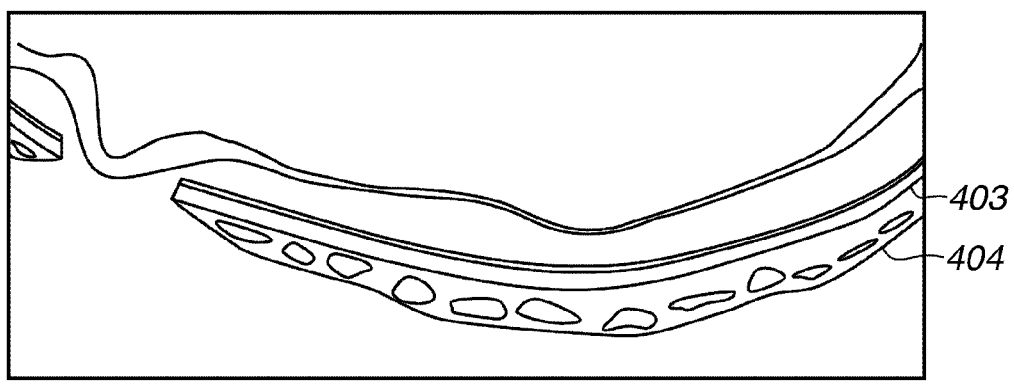
Figure 4C:
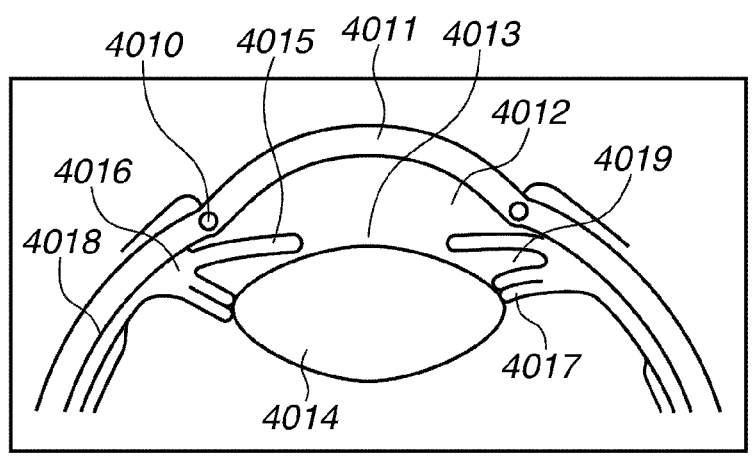

FIGS. 4A, 4B, and 4C illustrate examples of tomographic images imaged by the OCT 100 and produced by the signal processing unit 190.

FIG. 4A illustrates the tomographic image of a normal eye. FIG. 4B illustrates the tomographic image of myopia. Boundary of each layer such as a boundary 401 between a retinal pigment epithelial and a choroid and a boundary 402 between the choroid and a sclera is imaged. As illustrated in the figures, the tomographic image can be imaged in a broad range (in the transverse direction of the figure) and in a depth range (in the longitudinal direction thereof). If the tomographic image is displayed in the display area of the display unit 192, it is meaningless to display an area without a tomographic image. Therefore, in the present exemplary embodiment, a part of the tomographic image in the data loaded into the memory of the signal processing unit 190 is recognized and the tomographic image conforming to the size of the display area is segmented and displayed.

FIG. 4C illustrates an example of the tomographic image of the anterior segment acquired by imaging the subject's eye in the anterior segment mode. A Schlemm's canal 4010 is formed of a plurality of canals opened in an angulus iridocorneals. Aqueous humor flowing into an anterior chamber is discharged thereto. A cornea 4011 is a transparent membrane forming an outer membrane and an input of light ray. The cornea 4011 serves as a lens with a crystalline lens. An anterior chamber 4012 has a function of storing aqueous humor. The aqueous humor is transparent liquid providing nourishment for the anterior chamber and the crystalline lens, produced by a ciliary process, and keeps an intraocular pressure. A pupil 4013 is a round hole at the center of the iris and an inlet of light. A crystalline lens 4014 performs focusing adjustment along with a ciliary body. An iris 4015 includes musculus dilatator papillae and pupillary sphincter and adjusts the amount of light entering the eye according to brightness.

A ciliary body 4016 fixes the iris 4015 and changes the thickness of the crystalline lens by the tension and relaxation of a ciliary muscle to focus an image on the retina. The ciliary body 4016 produces aqueous humor. A zonule of Zinn (ciliary zonule) 4017 connects the ciliary body 4016 with the crystalline lens to support the crystalline lens. A choroid 4018 is rich in ciliary vas and pigment, provides nourishment for the retina and plays a role for a photo darkroom. A posterior chamber 4019 stores the aqueous humor as is the case with an anterior chamber.

Figure 5:
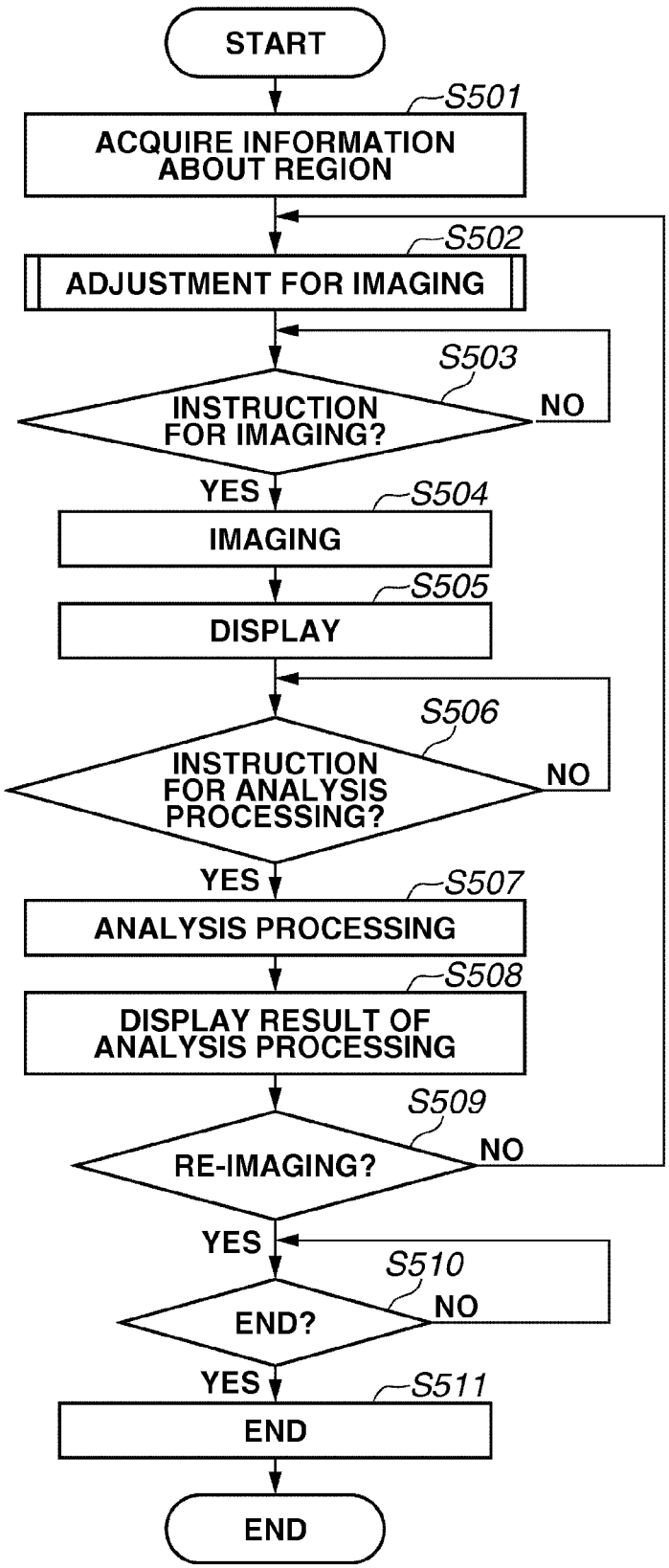
FIG. 5 is a flow chart indicating a flow of processing performed by the optical coherence tomography imaging apparatus.

The control processing of the optical coherence tomography imaging using the optical coherence tomography imaging apparatus is described below according to a flow chart illustrated in FIG. 5.

In step S501, the region acquisition unit 302 acquires an imaging target region. The imaging target region is acquired with reference to information about an imaging mode specified by the mode specifying unit 311 according to the input performed by the user operating the operation unit 311.

In step S502, the adjustment processing required for imaging is performed. The alignment of the apparatus with the subject's eye and the adjustment of focus position of the measuring beam are performed with the subject's eye arranged in the apparatus. The CG control unit 301 controls the difference in optical path length between the reference beam and the measuring beam by the control method according to the imaging target region. As described above, the adjustment may be performed by an automatic adjustment using feedback control based on an image or a manual adjustment. Alternatively, if the results of the automatic adjustment can be appropriately and manually adjusted, the adjustment can be effectively performed in a state desired by the user. The details of processing in step S502 are described below.

In step S503, imaging instructions are on standby with the adjustment completed. The control unit 200 is on standby until receiving an input indicating the imaging instructions from the operation unit 312 operated by the user. If the input is received, the processing promptly proceeds to step S504. The OCT 100 scans the imaging target region in the subject's eye using light of the wavelength-swept light source to produce a tomographic image. In step S505, the display control unit 191 causes the display unit 192 to display the tomographic image produced by imaging on the display unit 192. Needless to say, display in combination of the SLO image and the anterior segment image acquired at the time of the imaging allows an effective and detailed diagnosis through the image captured from a plurality of aspects.

In step S506, the control unit 200 waits for instructions given to the analysis processing unit 313 to analyze the acquired tomographic image and image groups. Instructions for analysis are performed based on the input by the user via the operation unit 312 as is the case with instructions for imaging. If the instructions are given, the analysis processing unit 313 starts analysis processing. As another exemplary embodiment, the analysis processing may be performed without the instructions. In this case, the analysis processing unit 313 is instructed to perform the analysis processing in response to the control unit 200 detecting the end of the imaging processing in step S504 and execute the processing in step S507. This eliminates an unnecessary operation and makes the processing effective if it is previously known that predetermined analysis processing is performed particularly in medical examination. In step S508, the display control unit 191 causes the display unit 192 to display the results of the analysis processing. The control unit 200 can omit the processing from the instructions for the analysis processing to the display of the analysis processing in steps S506 to S508 according to the setting. This setting is effective for diagnosis without requiring the analysis processing.

In step S509, the control unit 200 waits for instructions for re-imaging. If the control unit 200 is given the instructions for re-imaging by the operation unit 312, the control unit 200 instructs the OCT 100 to perform re-imaging and the processing proceeds to step S502. As another exemplary embodiment, the determination unit 310 determines whether the adjustment needs to be performed again and if the determination unit 310 determines that the adjustment is completed, it is effective that the processing is caused to proceed to the imaging processing in step S504.

In step S510, the control unit 200 waits for instructions for end. If the control unit 200 is given the instructions for end, the control unit 200 ends the imaging. If switching is performed between the left and right eyes or a subject is changed, the processing is performed again from step S501.

Figure 6:
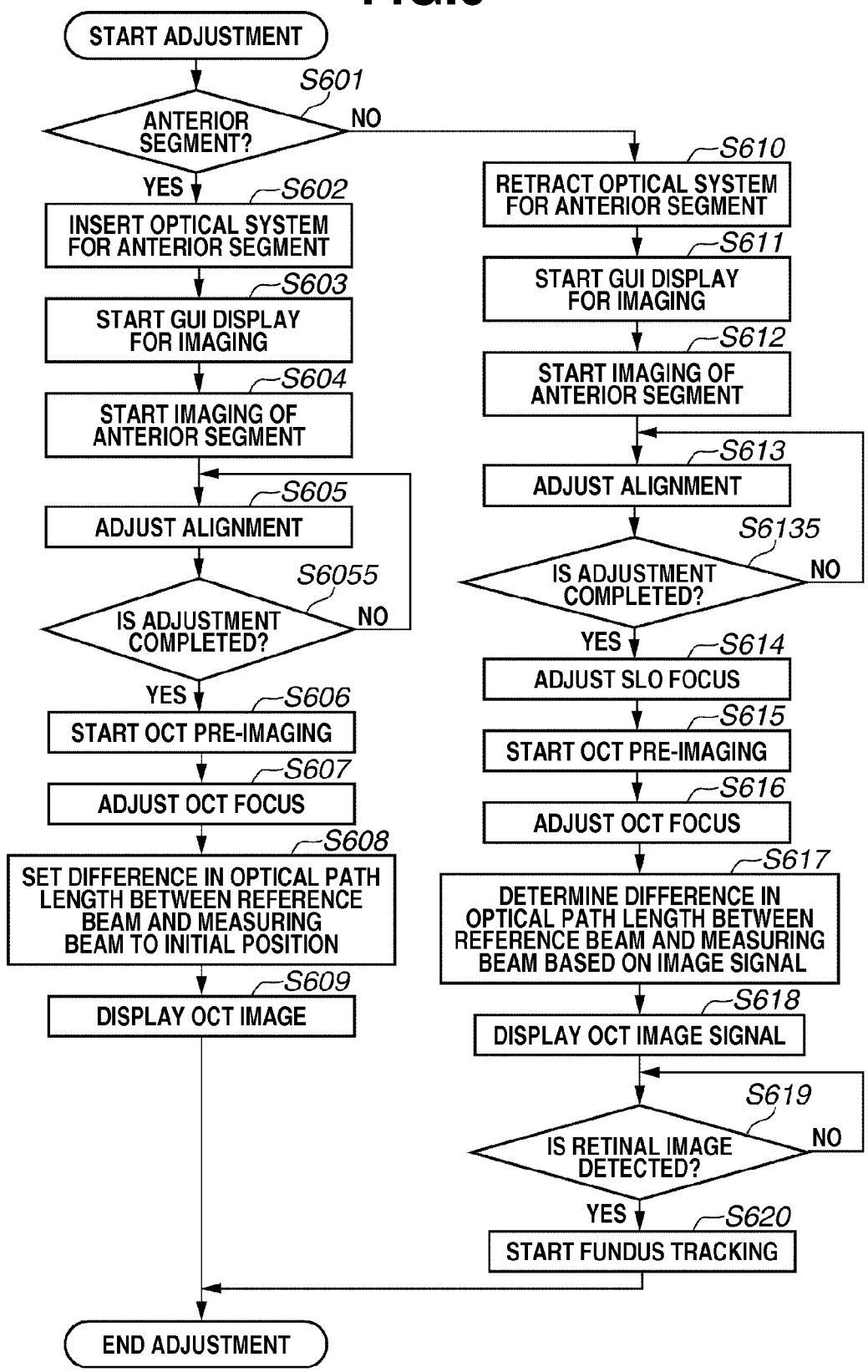
FIG. 6 is a flow chart indicating a flow of adjustment processing performed before imaging.

The flow of the adjustment processing for imaging according to the exemplary embodiment with reference to a flow chart illustrated in FIG. 6.

In step S601, the control unit 200 determines whether the anterior segment is an imaging target region. As described above, the processing may be determined using information about a region acquired by the region acquisition unit 302 or determined by the adapter detection unit whether the adapters for imaging the anterior segment are attached. Alternatively, the processing is determined using both to allow surely setting the imaging target region. If the control unit 200 determines that the anterior segment is the imaging target region (YES in step S601), the processing proceeds to step S602. If the control unit 200 determines that the posterior segment is the imaging target region (NO in step S601), the processing proceeds to step S610.

In step S602, if an optical system for imaging the anterior segment is not arranged in an imaging optical path due to influence of previous imaging, the optical system changing unit 304 controls the drive unit to insert the optical system into the imaging optical path.

In step S603, the display control unit 191 causes the display unit 192 to start displaying the GUI for imaging the anterior segment thereon. For example, information about the imaging target region set in step S501 is displayed. The GUI displayed on the display unit 192 is appropriately changed by the display control unit 191 according to progress in adjustment and imaging. For example, the control unit 200 acquires the adjustment state about a plurality of adjustment items according to progress in adjustment. The display control unit 191 causes the display unit 192 to display not only the tomographic image of the subject's eye but also the acquired plurality of adjustment states according to the specified imaging mode thereon. The details of the GUI are described below.

In step S604, the control unit 200 causes the anterior segment imaging unit 160 to start imaging the anterior segment. The anterior segment is imaged to manually or automatically adjust the alignment of the anterior segment with the optical coherence tomography imaging apparatus. If the tomographic image of the anterior segment is captured, a tomographic image position in the anterior segment is used by the user to specify the position.

In step S605, the stage unit 207 functioning as the alignment unit is driven to perform an alignment adjustment. Manual adjustment is performed by the operation unit 312 or a joy stick (not illustrated) moving the stage unit 207. Alternatively, the control unit 200 may automatically perform alignment using an image of the anterior segment.

In step S6055, the determination unit 310 determines whether the adjustment of alignment is completed. If the determination unit 310 determines that the adjustment of alignment is not completed (NO in step S6055), the control unit 200 drives the stage unit 207 to perform further adjustment. If the adjustment is manually performed, such determination processing is not performed.

In step S606, the OCT 100 starts OCT pre-imaging. The term pre-imaging refers to imaging performed for setting imaging condition and position before an actual imaging is performed. More specifically, the light source 101 is caused to emit light, the X and Y scanners are driven, the interference light is detected by the differential detector 129, and the tomographic image is produced by the signal processing unit 190. At this point, the focus of the OCT 100 and the coherence gate are not set, so that a targeted tomographic image has not always been acquired.

In step S607, the OCT focus control unit 307 controls the focus position of the OCT based on the image signal of the tomographic image.

In step S608, the CG control unit 301 sets the difference in optical path length between the reference beam and the measuring beam as an initial position. In the processing, an initial value corresponding to a predetermined imaging target region is stored in the storage unit 309 and the coherence gate stage 122 is driven through the drive control unit 180 to move the reference mirror 123 to the initial position corresponding to the initial value.

In step S609, the display control unit 191 causes the display unit 192 to display the signal of the tomographic image. The image data displayed here is the image data of the subject generated by the signal processing unit 190 based on the electric signal acquired by detecting the interference light with the difference in optical path length controlled according to the region.

In step S610, for the case of imaging the posterior segment, if the optical system for imaging the anterior segment is arranged in the imaging optical path due to influence of previous imaging, the optical system changing unit 304 controls the drive unit to retract the optical system from the imaging optical path.

In step S611, the display control unit 191 causes the display unit 192 to display the GUI for imaging the posterior segment thereon.

In step S612, the control unit 200 causes the anterior segment imaging unit 160 to start imaging the anterior segment similarly to step S604.

In step S613, the alignment adjustment is performed similarly to step S605.

In step S6135, the determination unit 310 performs the determination processing similarly to step S6055.

In step S614, the SLO focus control unit 308 adjusts the focus position of the SLO to focus on the fundus.

In step S615, the OCT 100 starts OCT pre-imaging similarly to step S606.

In step S616, the OCT focus control unit 307 sets the focus position of the OCT based on the focus position of the SLO.

In step S617, the CG control unit 301 determines the difference in optical path length between the reference beam and the measuring beam based on the image signal of the tomographic image. The CG control unit 301 controls the coherence gate stage 122 to move the reference mirror 123 and search for a position regarded as an appropriate difference in optical path length.

In step S618, the display control unit 191 causes the display unit 192 to display the signal of the tomographic image acquired by the signal processing unit 190.

In step S619, the determination unit 310 determines whether a retinal image is appropriately acquired. The determination is made as to whether the luminance value of the image is equal to or greater than a threshold value. Alternatively, the determination can be made as to whether an appropriate tomographic image is acquired based on a pattern matching according to the imaging target region.

In step S620, the control unit 200 causes the SLO 140 to start tracking for compensating the movement of the fundus based on the SLO image. Information about the movement of the fundus acquired by the tracking is appropriately input to the control unit 200 and the control unit 200 moves the position of the scanner of the OCT 100 and the SLO 140 so as to compensate the movement. The tracking is started as soon as the focus of the SLO 140 is adjusted in step S614 to allow the OCT to be effectively adjusted.

Figure 7:
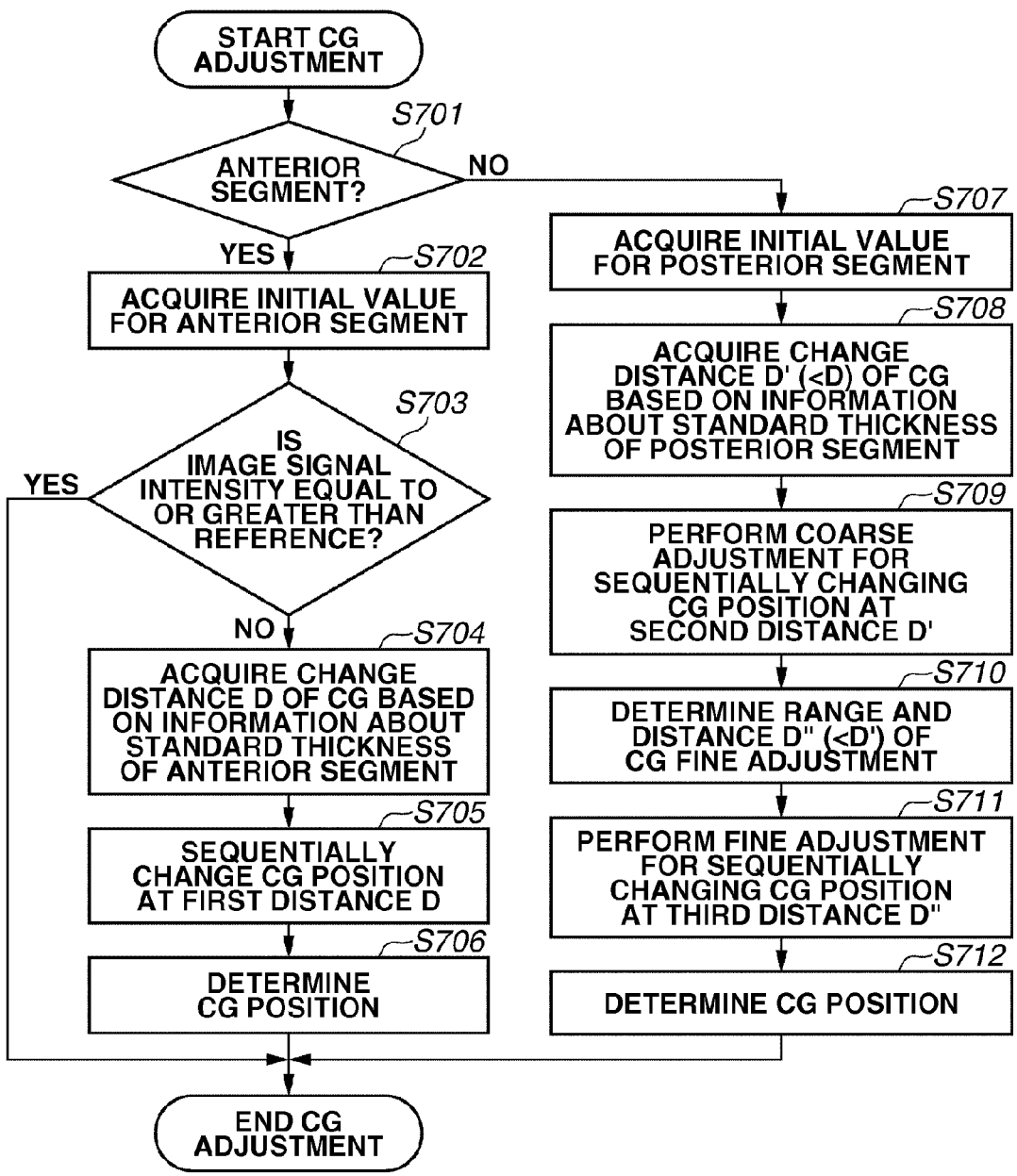
FIG. 7 is a flow chart indicating a flow of coherence gate adjustment processing.

The adjustment processing of the coherence gate according to an exemplary embodiment is described below with reference to a flow chart illustrated in FIG. 7. In the control illustrated in FIG. 7, in a case where the anterior segment is imaged, the CG control unit 301 sets an initial value and only if a criterion is not satisfied by the initial value, the mirror 123 is moved by a distance D to determine the difference in optical path length. In a case where the posterior segment is imaged, on the other hand, not only a coarse adjustment is performed in which the difference in optical path length is adjusted by a distance D' (<D) but also a fine adjustment is performed in which the difference in optical path length is adjusted by a distance D" (<D') to determine the difference in optical path length. This enables effective adjustment according to the imaging target region.

In step S701, the CG control unit 301 determines whether the anterior segment is imaged. The determination is similar to the one that is made in step S601.

In step S702, the CG control unit 301 acquires the initial value of the CG adjustment value for imaging the anterior segment. At this point, if a value, in which a value considering standard thickness information stored in the storage unit 309 is corrected based on the working distance measured in adjusting alignment in step S605, is acquired as an initial value, the coherence gate can be adjusted by the initial value according to the subject to allow reducing a probability that the processing is performed in step S704 and subsequent steps, enabling the adjustment to be made efficiently.

In step S703, the determination unit 310 acquires the tomographic image obtained with the mirror 123 arranged in a position according to the initial value. The determination unit 310 determines whether the luminance value of the tomographic image satisfies a reference. If the determination unit 310 determines that the luminance value satisfies the reference (YES in step S703), the adjustment of the coherence gate is completed.

In step S704, the control setting unit 303 acquires a change distance D of the difference in optical path length based on the standard thickness information of the anterior segment. The initial value considering the standard thickness information may be previously stored in the storage unit 309.

In step S705, the CG control unit 301 sequentially changes the position of the mirror 123 by the acquired distance D. The control unit 200 causes the OCT 100 to capture the tomographic image with the mirror 123 lies in each position.

In step S706, the determination unit 310 acquires a representative value of the luminance value of the tomographic image corresponding to each position of the mirror 123. The CG control unit 301 identifies the position of the mirror 123 corresponding to the tomographic image of which the representative value of the luminance value becomes maximized and moves the mirror 123 to such a position.

In a case where the posterior segment is imaged, on the other hand, in step S707, the CG control unit 301 acquires the initial value of the CG adjustment value for imaging the posterior segment from the storage unit 309.

In step S708, the control setting unit 303 acquires the change distance D' of the difference in optical path length based on information about the thickness of the posterior segment. In general, the posterior segment is smaller in thickness than the anterior segment, so that the change distance D' is smaller than the change distance D in a case where the anterior segment is imaged. If the change distance D is previously determined, the change distance D' smaller than the change distance D may be set.

In step S709, the CG control unit 301 sequentially changes the position of the mirror 123 by the acquired distance D'. The control unit 200 causes the OCT 100 to capture the tomographic image with the mirror 123 lies in each position. Along with the acquisition of the tomographic image, the determination unit 310 acquires a representative value of the luminance value of the tomographic image corresponding to each position of the mirror 123. The CG control unit 301 identifies the position of the mirror 123 corresponding to the tomographic image of which the representative value of the luminance value becomes maximized.

If the representative value is greater than a predetermined reference value, the movement of the mirror 123 can be temporarily stopped. In this case, the mirror 123 is moved in turn from the vicinity of the acquired initial position to allow the reduction of adjustment time.

Such a parallel processing between the imaging and the determination and the processing in which the adjustment is temporarily stopped according to the acquisition of the representative value greater than the reference value may be used for the adjustment in imaging the anterior segment.

In step S710, a predetermined range with such a position as a reference is set as a search range for the fine adjustment. Such a search range is smaller than that for the coarse adjustment in step S709. Therefore, the control setting unit 303 acquires the change distance D" of the position of the mirror 123 for searching the search range as a value smaller than the change distance D'.

In step S711, the CG control unit 301 sequentially changes the position of the mirror 123 by the acquired distance D". The control unit 200 causes the OCT 100 to capture a tomographic image with the mirror 123 set in each position.

In step S712, the determination unit 310 acquires a representative value of the luminance value of the tomographic image corresponding to each position of the mirror 123. The CG control unit 301 determines the position of the mirror 123 corresponding to the tomographic image of which the representative value becomes maximized.

The position of the coherence gate is adjusted by the predetermined distance even after the adjustment is performed to allow decreasing influence on image quality due to a change in the difference in optical path length occurring until the imaging is started after the adjustment is ended.

Figure 8:
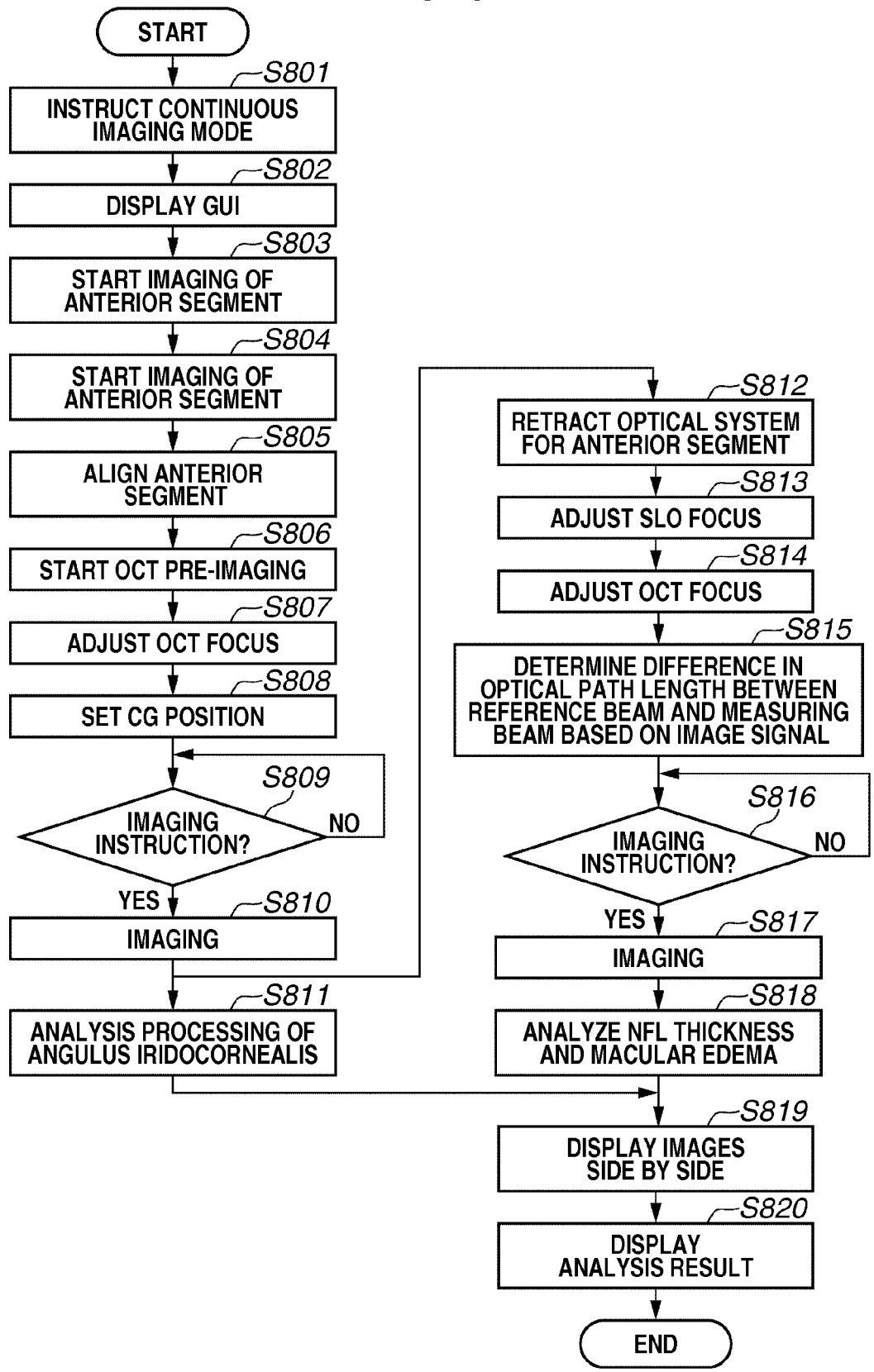
FIG. 8 is a flow chart indicating a flow of imaging processing in a continuous imaging mode.

Adjustment processing in a case where instructions of a continuous imaging mode are given is described below with reference to a flow chart illustrated in FIG. 8. The processing in steps S803 to S810 corresponds to that in steps S604, S605, S606, S607, and S608 in FIG. 6 and steps S503 and S810 in FIG. 5, respectively. The processing in steps S813, S814, S816, and S817 corresponds to that in steps S614 and S616 and steps S503 and S504, respectively.

In step S801, the determination unit 310 specifies the continuous imaging mode according to the user's operation input. The term "continuous imaging mode" refers to an imaging mode in which a plurality of imaging target regions is continuously imaged. If an imaging target object is the eye, an imaging mode for imaging both the anterior and posterior segments, for example, is available. In that imaging mode, accordingly as the imaging of one of the anterior and posterior segments is ended, at least a part of an imaging preparation for the other is started.

In step S802, the display control unit 191 starts the display control of the GUI for the continuous imaging. For the continuous imaging, the display control unit 191 causes the display unit 192 to display the GUI for imaging the one of the anterior and posterior segments before the one is imaged and causes the display unit 192 to change display to the GUI for imaging the next accordingly as the imaging of the one is ended. The display unit 192 performs display indicating the continuous imaging mode as the imaging mode irrespective of whichever imaging is being adjusted. Alternatively, if the region to have been imaged or the imaging mode and the region yet to be imaged or the imaging mode are displayed, which allows the user to recognize the order of imaging and reduces the possibility of erroneous imaging in a case where a plurality of imaging operations, particularly three imaging operations, are continuously performed.

In step S808, the CG control unit 301 adjusts the difference in optical path length between the reference beam and the measuring beam. The results of the adjustment are stored in the storage unit 309.

In step S811, the analysis processing unit 313 performs analysis processing of an angulus iridocorneals based on the tomographic image of the imaged anterior segment. The analysis processing unit 313 may perform analysis processing of the thickness of the angulus iridocorneals. Such analysis processing is performed by using a graphics processing unit (GPU) of the control unit 200, for example. The analysis processing of the tomographic image acquired by the tomographic imaging of the anterior segment is performed in parallel with the imaging to be started next before the tomographic imaging of the posterior segment is ended after the tomographic imaging of the anterior segment is ended to allow reducing a delay time from the imaging to the display of results of the analysis processing.

The adjustment processing for imaging the posterior segment in steps S812 to S815 is automatically shifted by the control unit 200 in response to the completion of the imaging in step S810. In the case of the continuous imaging mode, the alignment of the anterior segment is ended in step S805, so that control is performed with the alignment omitted.

In step S812, the optical system changing unit 304 retracts the optical system according to the end of the imaging similarly to step S610.

In step S813, the SLO focus control unit 308 starts adjusting the focus position of the measuring beam of the SLO 140 according to the end of the imaging. In step S814, the OCT focus control unit 307 starts adjusting the focus position of the measuring beam of the OCT 100 according to the end of the imaging. For the posterior segment, a signal from the OCT 100 is weak, so that a lookup table indicating a correspondence relationship between the position of the SLO focus and the position of an OCT focus lens is stored in the storage unit 309 and the focus position of the OCT is controlled based on the SLO focus information.

In step S815, the CG control unit 301 adjusts the CG according to the end of the imaging. The CG control unit 301 acquires the value of the difference in optical path length in imaging the anterior segment stored in step S808 from the storage unit 309 to compare the value with a standard value. The value of the initial value used in step S815 is changed only by a difference therebetween from a predetermined value.

In step S818, the analysis processing unit 313 performs analysis processing of the tomographic image of the posterior segment. This processing performs the detection processing of the thickness of each layer of a retina and a lesion such as macular edema. In a case where the analysis processing is performed using the GPU, the analysis processing may be performed in step S818 according to the end of the analysis processing in step S811.

In step S819, the display control unit 191 causes the display unit 192 to display the acquired tomographic images side by side. Displaying the tomographic images side by side improves a diagnostic efficiency of such a disease that appears on both regions such as the angulus iridocorneals of the anterior segment and the thickness of a retinal layer like diabetes mellitus, for example. Image display processing is performed before any of the analysis processing in steps S811 or S817 is ended to allow an imaging diagnostic before results of the analysis processing are output, thus reducing user's waiting time.

In step S820, the display control unit 191 causes the display unit 192 to display the acquired analysis results thereon.

Such processing can effectively execute the continuous imaging.

Figure 9:
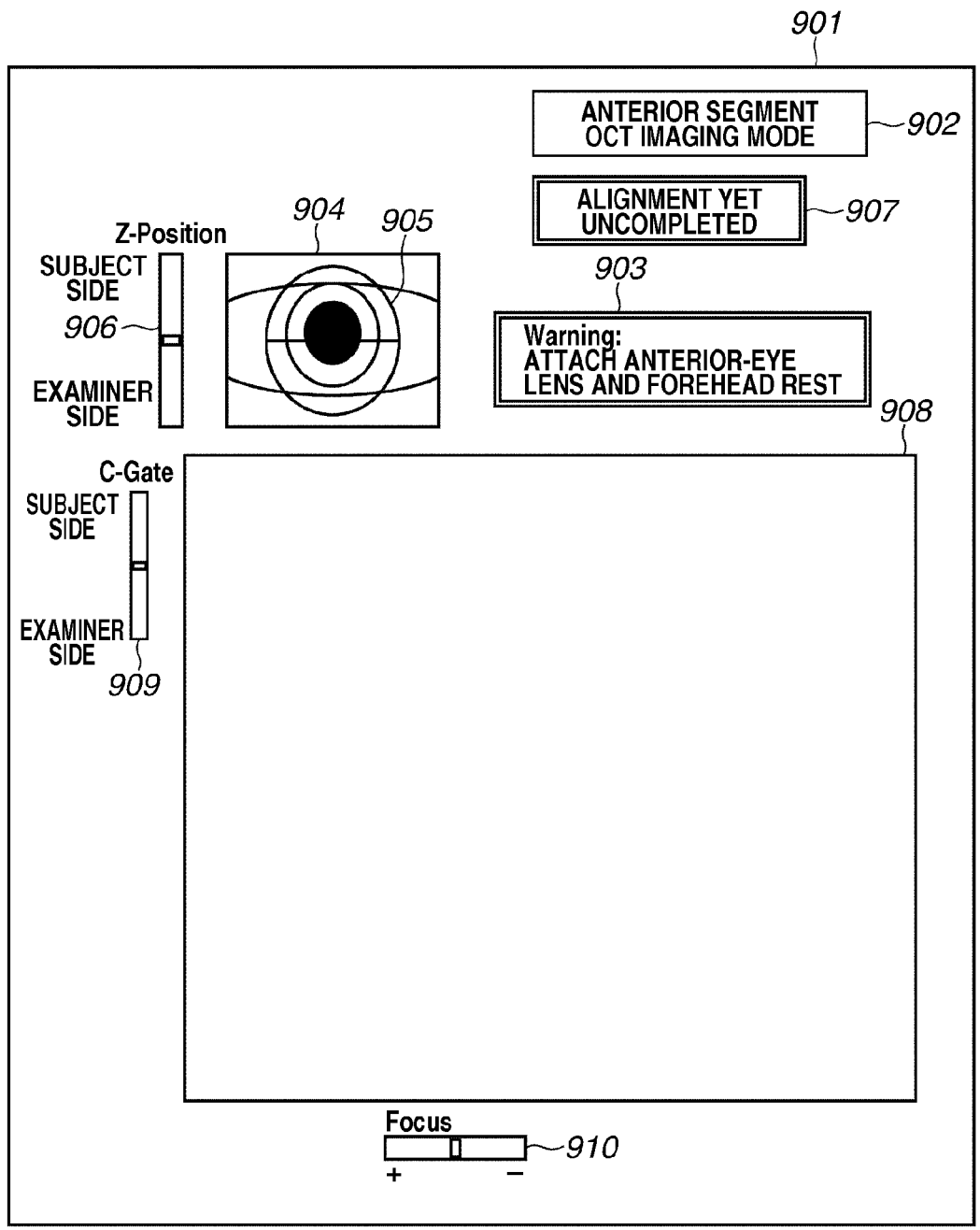
FIG. 9 illustrates an example of an imaging screen in an anterior segment OCT imaging mode.

FIG. 9 illustrates an example of the GUI displayed in imaging the anterior segment. A display screen 901 acquires and displays imaging support information, imaging setting information, or an image which is being captured in real time. The display screen 901 is displayed by the control of the display control unit 191 on the display unit 192.

An area 902 is a display use area where the imaging mode specified by the mode specifying unit 311 is displayed. In the case of the anterior segment imaging mode, characters of "Anterior segment OCT imaging mode" are displayed on the area 902. Alternatively, the imaging target region may be displayed by an icon which highlights the imaging target region on the eye image, instead of using the characters.

An area 903 displays the adjustment state regarding the adjustment items according to the imaging mode. As illustrated in FIG. 9, information about the adjustment state of the anterior-eye lens and the forehead rest is displayed as the adjustment items specific to the anterior segment imaging mode.

An area 907 is the one where the adjustment state about the adjustment items common among a plurality of the imaging modes is displayed. In FIG. 9, there are displayed characters indicating that alignment is not yet completed.

Unlike the area 902, the areas 903 and 907 are encompassed by double frames. This means that the adjustment is not yet completed. In a case where the completion of the adjustment of the adjustment items is displayed, on the other hand, an area is encompassed by a normal frame as is the case with the area 902. Thus, the display control unit 191 causes the display unit 192 to display a plurality of adjustment states by display forms indicating the adjustment items in which adjustment for the imaging of the anterior segment is completed or not completed and to highlight the adjustment items in which the adjustment is yet not completed. Such a highlight allows the user to recognize that the adjustment is not yet completed.

The area 903 displays the characters of "Warning." The characters are displayed in a case where the display control unit 191 determines that there is a difference between the information of the imaging mode displayed in the area 902 and the state of the adjustment item. For the imaging of the anterior segment, alignment cannot be accurately performed unless the adapter unit such as the anterior-eye lens and the forehead rest are attached to adjust the working distance and the optical system. Thus, the display control unit 191 causes the display unit 192 to display a plurality of adjustment states in the display form according to the imaging mode to which each of the plurality of adjustment states conforms and the warning if there is a difference between the information of the imaging mode and the state of the adjustment item. This allows strongly prompting the user to perform the adjustment.

An anterior-eye observation area 904 displays an image 905 of the anterior segment acquired by the anterior segment imaging unit 160.

An alignment slider 906 arranged near the anterior-eye observation area 904 is a GUI for manually adjusting the position of the optical head in the Z direction with respect to the subject's eye according to the user's operation. When the user moves the alignment slider 906 via the operation unit 312, the drive control unit 180 causes the stage unit 207 to move in the Z direction according to the moving direction. Clicking any point on the anterior-eye observation area 904 causes an XYZ table (not illustrated) to move the optical head 208 with the point as a center of the screen to align the optical head with the subject's eye.

An area 908 is a display area for confirming the tomographic image acquired by the OCT 100.

A CG slider 909 is a GUI for manually adjusting the position of the coherence gate of the OCT 100 according to the user's operation. When the user moves the CG slider 909 via the operation unit 312, the CG control unit 301 drives the coherence gate stage 122 via the drive control unit 180 to move the mirror 123 according to the moving direction.

A focus slider 910 is a GUI for manually adjusting the position of focus of the OCT 100 according to the user's operation. The OCT focus control unit 307 instructs the drive control unit 180 to move the focus lens in the illustrated direction to adjust the focus on the fundus. When the user moves the focus slider 910 via the operation unit 312, the OCT focus control unit 307 controls the drive control unit 180 according to the moving direction to change the position of the focus lens.

Figure 10:
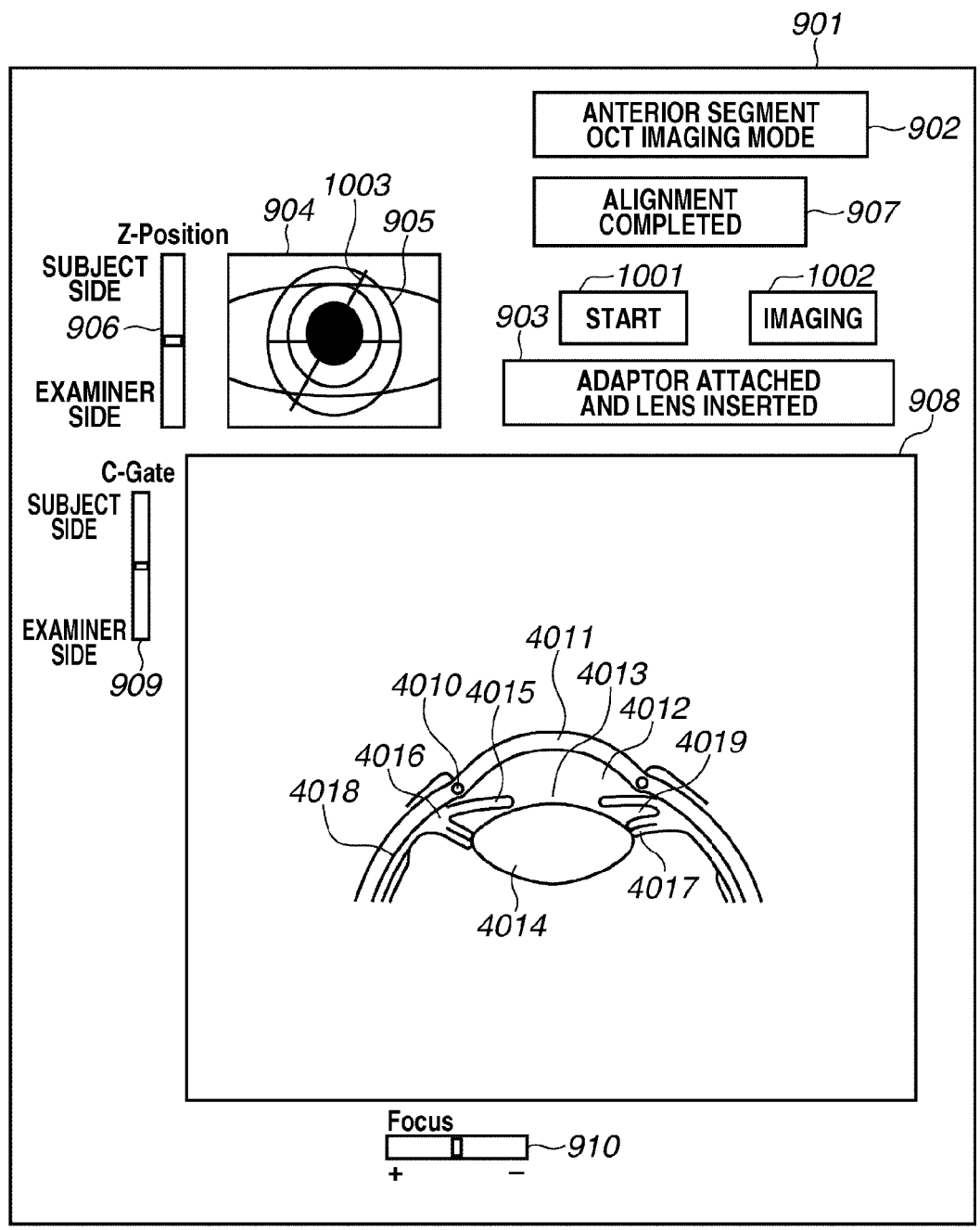
FIG. 10 illustrates another example of an imaging screen displayed in imaging the anterior segment.

FIG. 10 illustrates another example of the GUI displayed in imaging the anterior segment. In the state illustrated in FIG. 10, information indicating that the alignment is completed is displayed in the area 907 and encompassed by a single frame. Information indicating that the adapter is properly set is displayed in the area 903 in the characters of "Adaptor attached and lens inserted" and encompassed by a single frame. The area 908 displays the tomographic image of the anterior segment. A line segment 1003 is superimposed on the image 905 of the anterior segment in the anterior-eye observation area 904. The line segment 1003 indicates a scanning position (an imaging range) corresponding to the tomographic image displayed on the area 908. The user can freely set the position of the line segment 1003 via the operation unit 312. Setting may be performed so that scanning for the imaging is made in the position of the finally set line segment 1003.

FIG. 10 illustrates the state where the determination unit 310 determines that the imaging is ready. In this case, the display control unit 191 displays an imaging button 1002 accordingly as the determination unit 310 determines that the imaging is ready.

Pressing the imaging button 1002 when various adjustments are ended performs a desired imaging operation.

Pressing a start button 1001 starts the pre-imaging of the tomographic image to display the acquired image of the subject's eye on the area 908 in real time.

Figure 11:
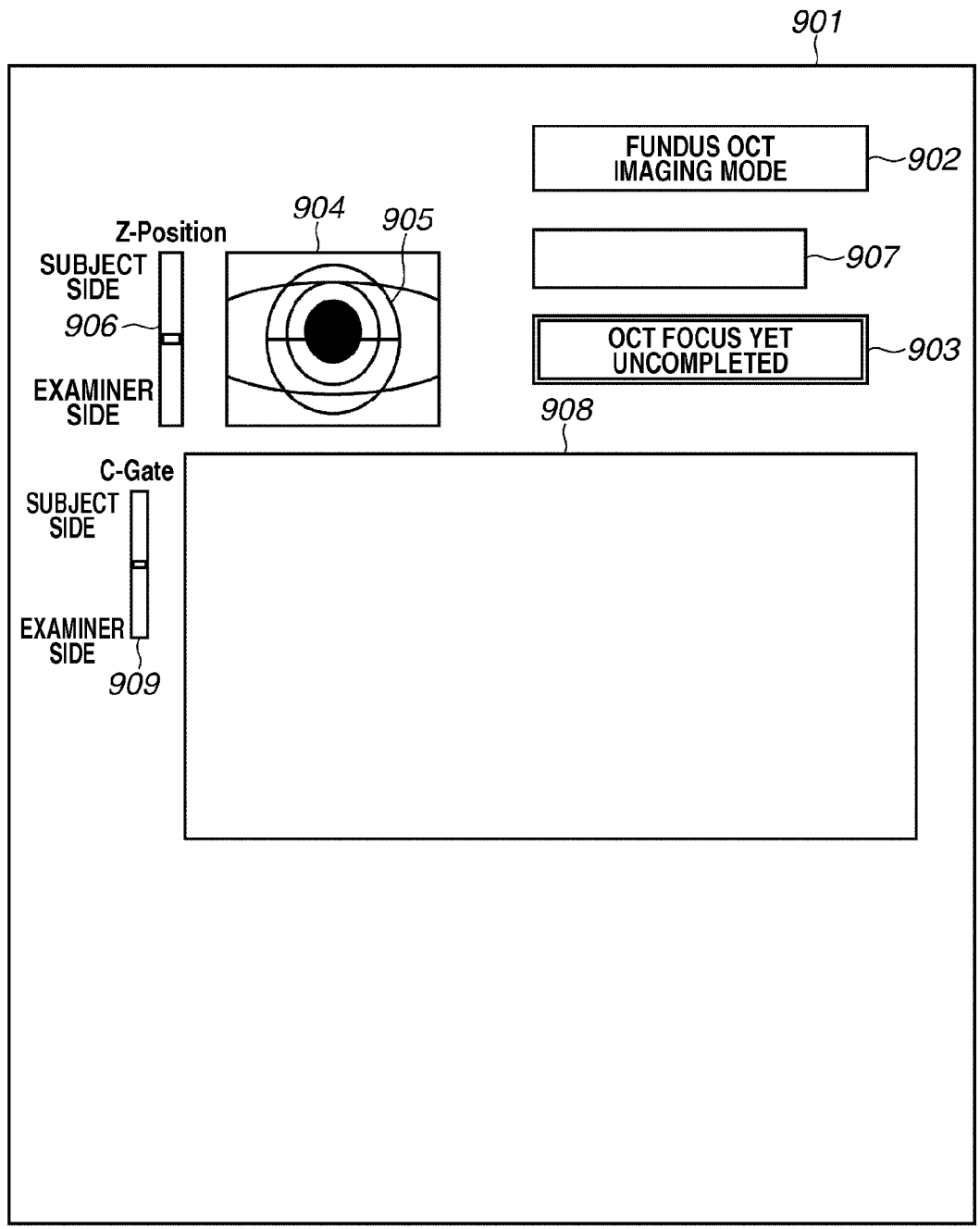
FIG. 11 illustrates an example of an imaging screen in imaging a fundus.

FIG. 11 illustrates an example of a screen in a case where a GUI for imaging in the posterior segment imaging mode is displayed on the display screen 901. Description of the portions similar to those described with reference to FIGS. 9 and 10 is not repeated.

The area 902 displays the imaging mode that the user specifies by the characters of "Fundus OCT imaging mode." The characters indicating that the focus of the OCT is not yet completed are displayed in the area 903 and encompassed by double frames indicating that adjustment is not yet completed. The GUI in a case where the automatic adjustment mode is not turned off is displayed. In this case, the area 907 does not display information indicating that the adjustment of alignment is completed to improve user's operability and information viewability.

Figure 12:
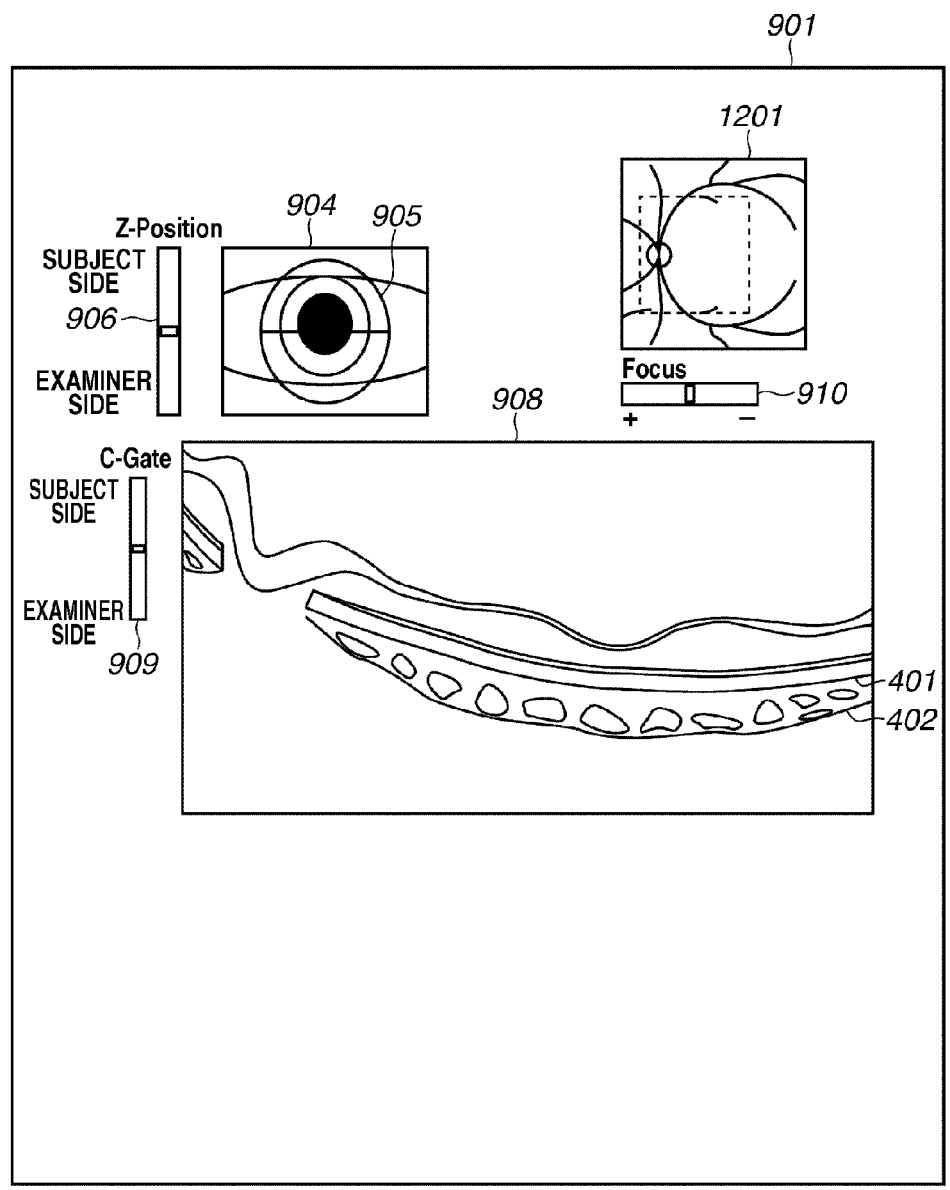
FIG. 12 illustrates another example of an imaging screen in imaging the fundus.

FIG. 12 illustrates an example of a GUI for imaging in the posterior segment imaging mode.

An area 1201 is the one that displays a two-dimensional fundus image acquired by the SLO 140.

Similarly to FIG. 11, also in FIG. 12, the GUI in a case where the automatic adjustment mode is not turned off is displayed. In this case, information indicating that the adjustment of alignment is completed is not displayed to improve user's operability and information viewability. FIG. 12 illustrates a state where the tomographic image of the fundus is displayed, and information about an imaging target region does not need to be displayed, so that the display of the area 902 is omitted from the screen.

Figure 13:
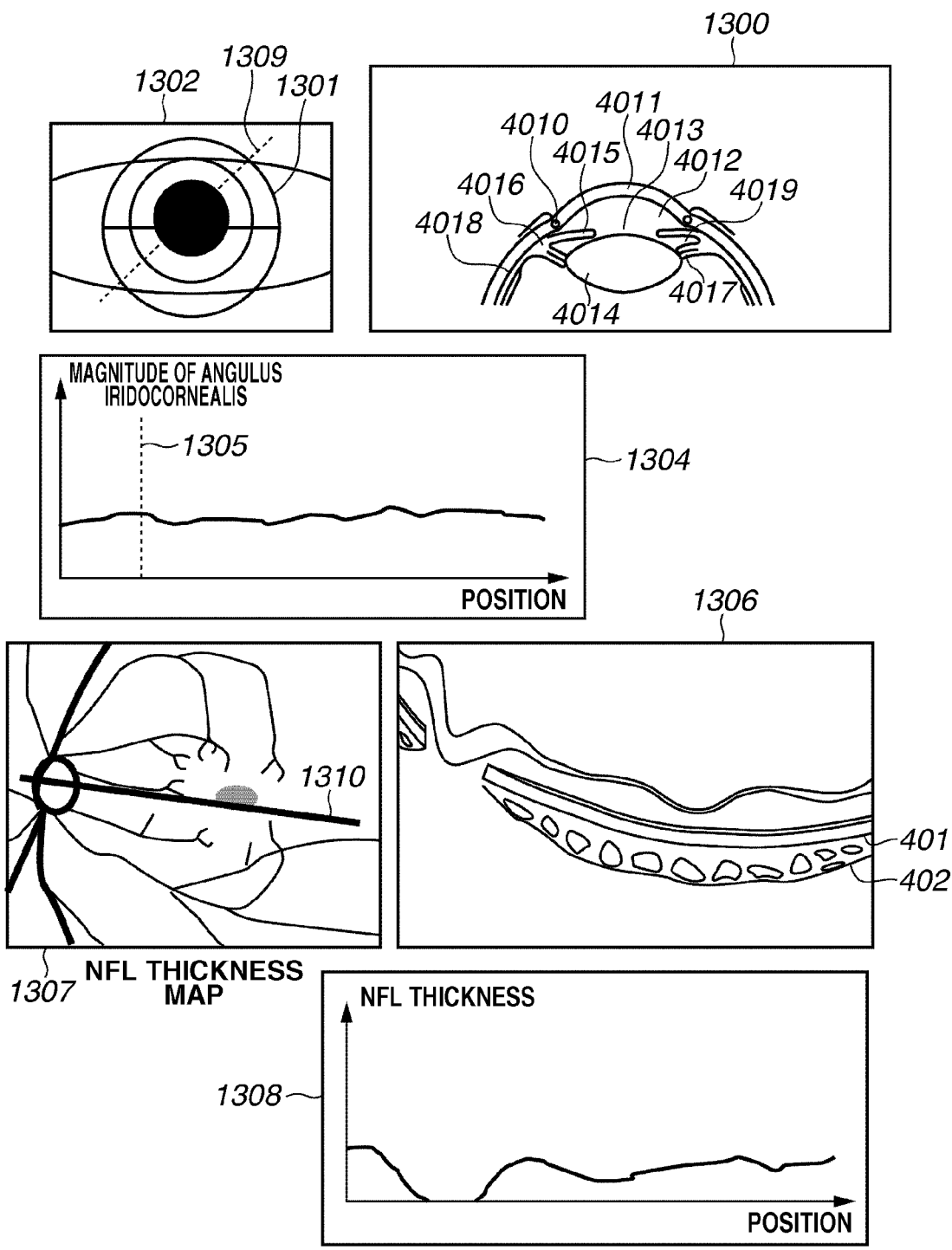
FIG. 13 illustrates examples of display screens for analysis results.

FIG. 13 illustrates examples of display screens on the results of the analysis processing in selecting the continuous imaging. The display screens can also be used when the anterior and posterior segments of the same subject's eye are imaged.

An area 1300 is the one that displays the tomographic image of the anterior segment.

A planar image 1301 of the anterior segment acquired by the imaging unit 160 is displayed in an area 1302. In the area 1302, a scanning position corresponding to the tomographic image of the anterior segment is indicated by a dotted line segment 1309. For the sake of viewability, the length of the line segment does not exactly agree with the scanning range. Needless to say, if only the position corresponding to the scanning range is indicated by a solid line, a correspondence relationship with the imaging range becomes easily understood.

An area 1304 indicates a graph about the size of an angulus iridocorneals being one of the results acquired by the analysis processing unit 313 analyzing the tomographic image of the anterior segment. The ordinate of the graph represents the magnitude of the angulus iridocorneals. The magnitude of the angulus iridocorneals is represented with a position, taken as angular components of a polar coordinate centering a pupil, as the abscissa. A line segment 1305 corresponds to the imaging position of the tomographic image indicated by the area 1300. The line segment 1305 also corresponds to the line segment 1309 indicating a scanning position. The user may operate the operation unit 312 to allow changing any one position of the tomographic image and line segments 1309 and 1305. The other image or line segment moves to a corresponding position along with the change. This allows comparing the tomographic image with the angulus iridocorneals and referring thereto.

An area 1306 displays the tomographic image of the posterior segment. An area 1307 displays the planar image of the fundus imaged by the SLO. A layer thickness map of a specific layer superimposed on the fundus image in the area 1307 can be displayed thereon. The display control unit 191 appropriately selects whether to display the layer thickness map and the layer to be displayed from the analysis results in the storage unit 309 based on the user's operation of the operation unit 312 and causes the display unit 192 to perform display. An area 1308 displays a graph indicating the layer thickness map of the specific layer in the tomographic image displayed in the area 1306. In the graph, the ordinate represents the layer thickness and the abscissa represents a position in the scanning direction B of the tomographic image. In the area 1307, a line segment corresponding to the scanning position and range of the tomographic image displayed in the area 1306 is rendered by a line segment 1310. The display control unit 191 selects the layer to be displayed in the areas 1307 and 1308 based on the user's input to the operation unit 312.

The user operates any one of the position of the segment 1310, the tomographic image, and the layer thickness to be displayed via the operation unit 312 to change other pieces of information along therewith. This enables an easy comparison with the corresponding relationship kept among the scanning position, the tomographic image, the layer thickness map, and the graph about the layer thickness in the specific tomographic image.

Thereby, displaying together the anterior-segment image and the analysis results thereof and the posterior-segment image and the analysis results thereof makes it easy to totally compare the abnormalities of the anterior and posterior segments with each other with respect to a specific disease.

Figure 14:
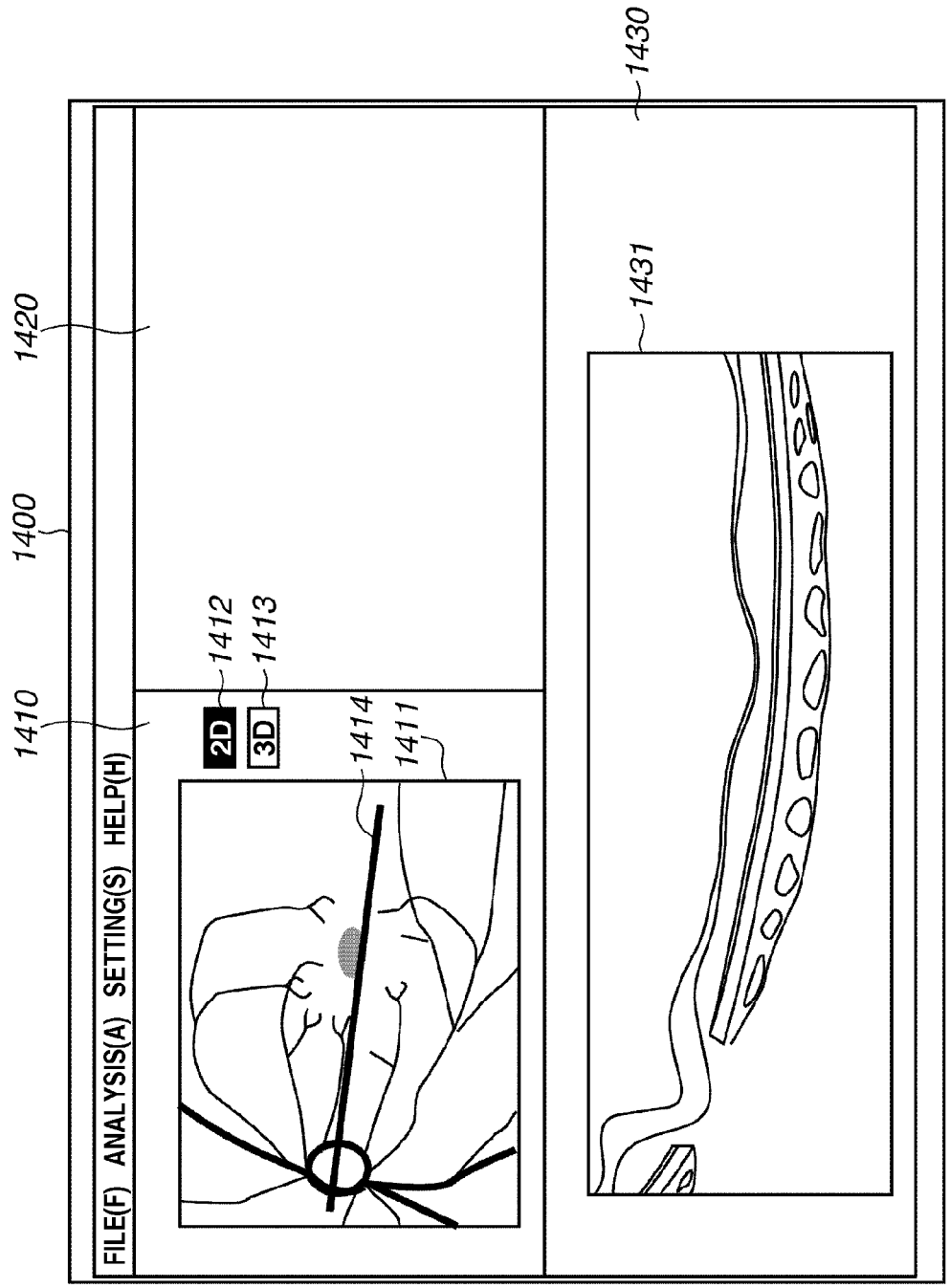
FIG. 14 illustrates another example displayed on a display unit.

FIG. 14 illustrates an example displayed by the display unit 192 according to the present exemplary embodiment. In FIG. 14, a tomographic image 1431 captured in a two-dimensional (2D) imaging mode is displayed in an area 1430.

In the present exemplary embodiment, the OCT 100 having a deep imaging range clips the tomographic image at a predetermined depth from the position of the coherence gate and displays the tomographic image. Although a display area for the tomographic image 1431 lies under an area 1411 in which the fundus image is displayed, the display area 1431 may lie over the area 1411. The tomographic image is displayed in an area over the area 1411 or the area 1431 lying under the area 1411 to allow displaying the tomographic image with a wide angle of view without reduction, thus making it easy for the user to observe the tomographic image. An area 1420 displays information about the apparatus and the subject.

As described above, according to the present exemplary embodiment, the tomographic image with a wide angle of view acquired by the SS-OCT can be effectively displayed. If a tomographic image cannot be displayed in a previously prepared display area for the tomographic image, the tomographic image is displayed in an enlarged area, so that the tomographic image can be displayed without impairing resolution. In addition, if a tomographic image cannot be displayed in a previously prepared display area for the tomographic image, the tomographic image is displayed with the area scrolled to allow displaying the tomographic image whose part is desired to be observed.

For example, the SS-OCT is capable of further extending the imaging range in the depth direction as compared with a convention OCT, the SS-OCT can also be used for tomographically imaging not only a retina but also the anterior segment, for example.

Figure 15:
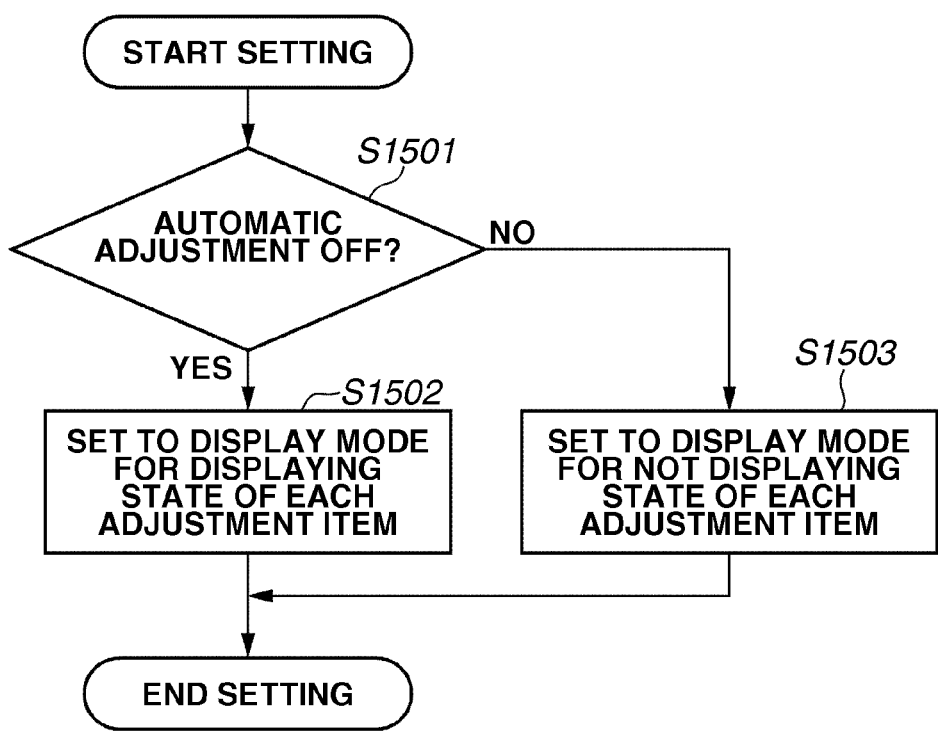
FIG. 15 is a flow chart indicating a flow of setting processing in a display mode.

The setting of the automatic adjustment is described below according to a flow chart illustrated in FIG. 15.

In step S1501, the control setting unit 303 determines whether the automatic adjustment is turned off. The automatic adjustment is set by the mode specifying unit 311 based on the operation input via the operation unit 312. If the control setting unit 303 determines that the automatic adjustment is turned off (YES in step S1501), the processing proceeds to step S1502. Otherwise (NO in step S1501), the processing proceeds to step S1503.

In step S1502, if the setting is not automatically performed, the control setting unit 303 sets a display mode for displaying information indicating that the adjustment of adjustment items is completed in which the determination unit 310 determines that the adjustment of adjustment items related to the setting is completed. The control setting unit 303 sets the display mode to the display control unit 191.

In step S1503, the control setting unit 303 sets a display mode not for displaying information indicating that the adjustment of adjustment items, whose adjustment is determined as being completed, is completed. The control setting unit 303 sets the display mode to the display control unit 191. Since it is insignificant to notify the user of the adjustment state of the completed adjustment items, the effective use of the screen area and the viewability of information are improved.

If the automatic adjustment of alignment, focus, and coherence gate is turned off by the mode specifying unit 311, the control setting unit 303 instructs the stage unit 207 functioning as the alignment unit, the adapter detection units illustrated in FIG. 2, the OCT focus control unit 307, and the CG control unit 301 not to perform the automatic adjustment. The control setting unit 303 can perform setting as to whether a plurality of adjustment items is individually and automatically adjusted. At this point, a determination as to whether the adjustment is completed does not need to be ended while controlling not to automatically perform the adjustment. Needless to say, the control setting unit 303 can instruct the determination unit 310 not to perform the determination processing itself.

According to the exemplary embodiment of the present invention, the difference in optical path length can be controlled by a method suited to the imaging target object to allow an image good in image quality to be acquired by a quick adjustment.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-082685 filed Mar. 30, 2012, which is hereby incorporated by reference herein in its entirety.

What is claimed is:

1. An optical coherence tomography imaging apparatus that acquires a tomographic image from interference light between a reference beam and a measuring beam obtained via an object, the optical coherence tomography imaging apparatus comprising:

an acquisition unit configured to acquire information indicating an imaging target region;

a control unit configured to control to set a first difference in optical path length between the reference beam and the measuring beam and adjust the first difference in optical path length at first intervals when the information indicates a first imaging target region, and to set a second difference in optical path length between the reference beam and the measuring beam and adjust the second difference in optical path length at second intervals smaller than the first intervals when the information indicates a second imaging target region; and a signal processing unit configured to generate image data of the object based on an electrical signal obtained by detecting the interference light with the difference in optical path length controlled by the control unit.

2. The optical coherence tomography imaging apparatus according to claim 1, wherein the control unit controls to set the first difference in optical path length to a pre-designated value with respect to the first imaging target region and controls to adjust the second difference in optical path length based on the signal of the interference light with respect to the second imaging target region.

3. The optical coherence tomography imaging apparatus according to claim 1, further comprising a determination unit configured to determine whether the image data generated by the signal processing unit satisfies a specific reference in a case where the first difference in optical path length is set to become a pre-designated value with respect to the first imaging target region, wherein, if the determination unit determines that the image data does not satisfy the specific reference, the control unit controls to adjust the first difference in optical path length based on the signal of the interference light obtained while sequentially changing the first difference in optical path length.

4. The optical coherence tomography imaging apparatus according to claim 1, wherein the first imaging target region is an anterior segment and the second imaging target region is a posterior segment.

5. The optical coherence tomography imaging apparatus according to claim 3, wherein the determination unit determines whether an intensity of a representative value of pixel values of the image data is equal to or greater than a specific threshold.

6. The optical coherence tomography imaging apparatus according to claim 1, wherein the control unit controls to set the first or second difference in optical path length to an initial value according to the first imaging target region or the second imaging target region.

7. The optical coherence tomography imaging apparatus according to claim 6, further comprising a storage unit configured to store, for each subject, a value indicating the difference in optical path length determined for each imaging target region of the subject.

8. The optical coherence tomography imaging apparatus according to claim 1, wherein the control unit controls to adjust the second difference in optical path length at the second intervals and third intervals smaller than the second intervals in the second imaging target region.

9. The optical coherence tomography imaging apparatus according to claim 4, further comprising a specifying unit configured to specify execution of a continuous imaging mode which is an imaging mode for imaging both of the anterior segment and the posterior segment and in which, accordingly as imaging one of the anterior segment and the posterior segment is ended, a preparation for imaging another is started.

10. The optical coherence tomography imaging apparatus according to claim 9, further comprising another control unit configured to shift imaging to a mode for imaging the posterior segment accordingly as the imaging of the anterior segment is ended when the continuous imaging mode is specified.

11. The optical coherence tomography imaging apparatus according to claim 9, further comprising a focus control unit configured to start adjusting a focus position of the measuring beam accordingly as tomographic imaging of the anterior segment is ended.

12. The optical coherence tomography imaging apparatus according to claim 9, further comprising an analysis processing unit configured to start analysis processing of a tomographic image obtained by tomographically imaging the anterior segment before tomographic imaging of the posterior segment is ended after tomographic imaging of the anterior segment is ended.

13. The optical coherence tomography imaging apparatus according to claim 9, wherein the specifying unit is capable of specifying one of a first mode which is transferred to an imaging mode of the posterior segment accordingly as imaging of the anterior segment is ended and a second mode which is transferred to an imaging mode of the anterior segment accordingly as imaging of the posterior segment is ended.

14. The optical coherence tomography imaging apparatus according to claim 1, further comprising a change unit configured to set either the first or the second difference in optical path length by changing a position of a reference minor in a reference optical path according to control of the control unit.

15. The optical coherence tomography imaging apparatus according to claim 1, further comprising:

a light source;

a light path division unit configured to divide an optical path for transmitting light emitted from the light source into a reference optical path and a measuring optical path;

a light interference unit configured to interfere the reference beam passing through the reference optical path with the measuring beam passing through the measuring optical path; and a detector configured to detect the interference light.

16. The optical coherence tomography imaging apparatus according to claim 15, wherein the light source is a wavelength-swept light source capable of varying wavelength.

17. The optical coherence tomography imaging apparatus according to claim 15, further comprising a display control unit configured to display image data generated by the signal processing unit, based on an interference component of the detected light.

18. A method for controlling an optical coherence tomography imaging apparatus that acquires a tomographic image from interference light between a reference beam and a measuring beam obtained via an object, the method comprising:

acquiring information indicating an imaging target region;

controlling to set a first difference in optical path length between the reference beam and the measuring beam and adjust the first difference in optical path length at first intervals when the information indicates a first imaging target region, and to set a second difference in optical path length between the reference beam and the measuring beam and adjust the second difference in optical path length at second intervals smaller than the first intervals when the information indicates a second imaging target region; and generating image data of the object based on an electrical signal obtained by detecting the interference light with the difference in optical path length controlled in the controlling step.

* * * * *